(12) United States Patent
Kreuzer

(10) Patent No.: US 10,646,206 B1
(45) Date of Patent: May 12, 2020

(54) MEDICAL DIAGNOSTIC ULTRASOUND IMAGING SYSTEM AND METHOD FOR COMMUNICATING WITH A SERVER DURING AN EXAMINATION OF A PATIENT USING TWO COMMUNICATION CHANNELS

(71) Applicant: Imorgon Medical LLC, San Mateo, CA (US)

(72) Inventor: Lloyd B. Kreuzer, The Sea Ranch, CA (US)

(73) Assignee: Imorgon Medical LLC, San Mateo, CA (US)

( * ) Notice: Subject to any disclaimer, the term of this patent is extended or adjusted under 35 U.S.C. 154(b) by 0 days.

(21) Appl. No.: 16/244,805

(22) Filed: Jan. 10, 2019

(51) Int. Cl.
*A61B 8/00* (2006.01)
*G16H 30/20* (2018.01)
*A61B 8/08* (2006.01)
*G16H 40/63* (2018.01)

(52) U.S. Cl.
CPC .............. *A61B 8/565* (2013.01); *A61B 8/465* (2013.01); *A61B 8/5292* (2013.01); *G16H 30/20* (2018.01); *A61B 8/4477* (2013.01); *G16H 40/63* (2018.01)

(58) Field of Classification Search
CPC ....... A61B 8/565; A61B 8/5292; A61B 8/465; G16H 10/60; G16H 15/00; G16H 40/63; G06F 19/321; G06Q 50/24
See application file for complete search history.

(56) References Cited

U.S. PATENT DOCUMENTS

| | | |
|---|---|---|
| 5,997,478 A | 12/1999 | Jackson et al. |
| 6,032,120 A | 2/2000 | Rock et al. |
| 6,129,671 A | 10/2000 | Hastings |
| 6,287,257 B1 | 9/2001 | Matichuk |
| 6,490,684 B1 | 12/2002 | Fenstemaker et al. |
| 6,514,201 B1 | 2/2003 | Greenberg |
| 6,524,245 B1 | 2/2003 | Rock et al. |
| 7,103,776 B1 | 9/2006 | Hall |
| 2002/0082850 A1 | 6/2002 | Panelli |
| 2003/0066050 A1 | 4/2003 | Wang |

(Continued)

OTHER PUBLICATIONS

Oracle Communications WebRTC Session Controller System Administrator Guide, Release 7.0, Nov. 2013 (Year: 2013).*

(Continued)

*Primary Examiner* — Boniface N Nganga
(74) *Attorney, Agent, or Firm* — Brinks Gilson & Lione

(57) ABSTRACT

A medical diagnostic ultrasound imaging system and method are provided for communicating with a server during an examination of a patient using first and second communication channels. Communication between the controller and the server via the second communication channel occurs within a predetermined amount of time. In one embodiment, the controller of the medical diagnostic ultrasound imaging system is configured to send and receive different information via the first communication channel than via the second communication channel. In another embodiment, communication between the controller and the server via the second communication channel is faster than communication between the controller and the server via the first communication channel. Other embodiments are presented, and each embodiment can be used alone or in combination with each other.

16 Claims, 22 Drawing Sheets

(56) References Cited

U.S. PATENT DOCUMENTS

| | | |
|---|---|---|
| 2003/0154102 A1 | 8/2003 | Panelli |
| 2003/0229514 A2 | 12/2003 | Brown |
| 2004/0114714 A1 | 6/2004 | Minyard |
| 2004/0122787 A1 | 6/2004 | Avinash |
| 2004/0141661 A1 | 7/2004 | Hanna |
| 2004/0146221 A1 | 7/2004 | Siegel |
| 2004/0204649 A1 | 10/2004 | Ramraj et al. |
| 2005/0049495 A1 | 3/2005 | Sumanaweera |
| 2005/0080330 A1 | 4/2005 | Masuzawa |
| 2005/0096539 A1 | 5/2005 | Leibig |
| 2005/0113690 A1 | 5/2005 | Halmann |
| 2005/0265267 A1 | 12/2005 | Hwang |
| 2006/0242148 A1 | 10/2006 | Rothpearl |
| 2006/0271400 A1 | 11/2006 | Clements |
| 2007/0016034 A1 | 1/2007 | Donaldson |
| 2007/0043597 A1 | 2/2007 | Donaldson |
| 2007/0168339 A1* | 7/2007 | Vezina ............... G09B 7/00 |
| 2008/0070225 A1 | 3/2008 | Vezina |
| 2008/0194950 A1 | 8/2008 | Mejia |
| 2008/0319275 A1 | 12/2008 | Chiu |
| 2009/0024028 A1 | 1/2009 | Washburn |
| 2009/0028410 A1 | 1/2009 | Shimazaki |
| 2009/0274384 A1 | 11/2009 | Jakobovits |
| 2010/0318667 A1 | 12/2010 | Miller |
| 2011/0131573 A1* | 6/2011 | Antony ............... G06F 3/023 |
| | | 718/1 |
| 2014/0022277 A1 | 1/2014 | Takeda |
| 2015/0149565 A1* | 5/2015 | Ahmed ............... H04L 65/403 |
| | | 709/206 |
| 2015/0313578 A1 | 11/2015 | Yu |
| 2015/0335315 A1 | 11/2015 | Choi |
| 2016/0113627 A1 | 4/2016 | Lee |
| 2016/0302666 A1 | 10/2016 | Shaya |
| 2017/0206322 A1 | 7/2017 | Kumar |
| 2019/0015080 A1 | 1/2019 | Kreuzer |

OTHER PUBLICATIONS

Office Action in U.S. Appl. No. 15/650,240, dated Jun. 25, 2019, 23 pages.
International Search Report dated Aug. 23, 2018 for International Application No. PCT/US2018/040069.
Written Opinion dated Aug. 23, 2018 for International Application No. PCT/US2018/040069.
Non-Final Rejection dated Aug. 31, 2018 in U.S. Appl. No. 15/650,240.
Final Rejection dated Feb. 8, 2018 in U.S. Appl. No. 15/650,240.
Non-Final Rejection dated Aug. 31, 2017 in U.S. Appl. No. 15/650,240.

* cited by examiner

DICOM Modality Worklist

| Patient Name | Patient Medical Number | Reason for Study | Study Date Time |
|---|---|---|---|
| Smith, John | 1234567 | Pain in abdomen | 12/4/17 10:45 AM |
| Doe, Jane | 8901234 | Pain in abdomen | 12/4/17 11:45 AM |

Start Study    Cancel

Smith, John 6/12/1950 MRN 123456

Prior Study list

| Date | Accession # | Indication | Referring |
|---|---|---|---|
| 5/3/2013 | 89743 | Pain in abdomen | Dr Jones |
| 9/17/2013 | 23807 | Pain in abdomen | Dr Jones |

- Order
- Report
- Images
- Measured Values
- Trended Values

MEDICAL DIAGNOSTIC ULTRASOUND IMAGING SYSTEM AND METHOD FOR COMMUNICATING WITH A SERVER DURING AN EXAMINATION OF A PATIENT USING TWO COMMUNICATION CHANNELS

BACKGROUND

A medical diagnostic ultrasound imaging system is used to conduct an ultrasound examination of a patient. Medical diagnostic ultrasound imaging systems are sometimes connected to a network, and information can be communicated to and from a server in the network before, during, or after the examination. For example, the medical diagnostic ultrasound imaging system can receive a list of scheduled patients from a study scheduling server before the examination, and the medical diagnostic ultrasound imaging system can store captured ultrasound images in an image server before, during, or after an examination.

BRIEF DESCRIPTION OF THE DRAWINGS

FIG. 4 is a screen shot of an exemplary DICOM modality worklist used to illustrate an embodiment.

FIG. 5 is a screen shot of an exemplary patient input screen of an embodiment.

FIG. 10 is a screen shot of an embodiment of a prior study list.

FIG. 13 is a screen shot of a display device of a medical diagnostic ultrasound imaging system of an embodiment in which an ultrasound image and a patient worksheet are simultaneously displayed on the display device.

DETAILED DESCRIPTION

Figure 1:
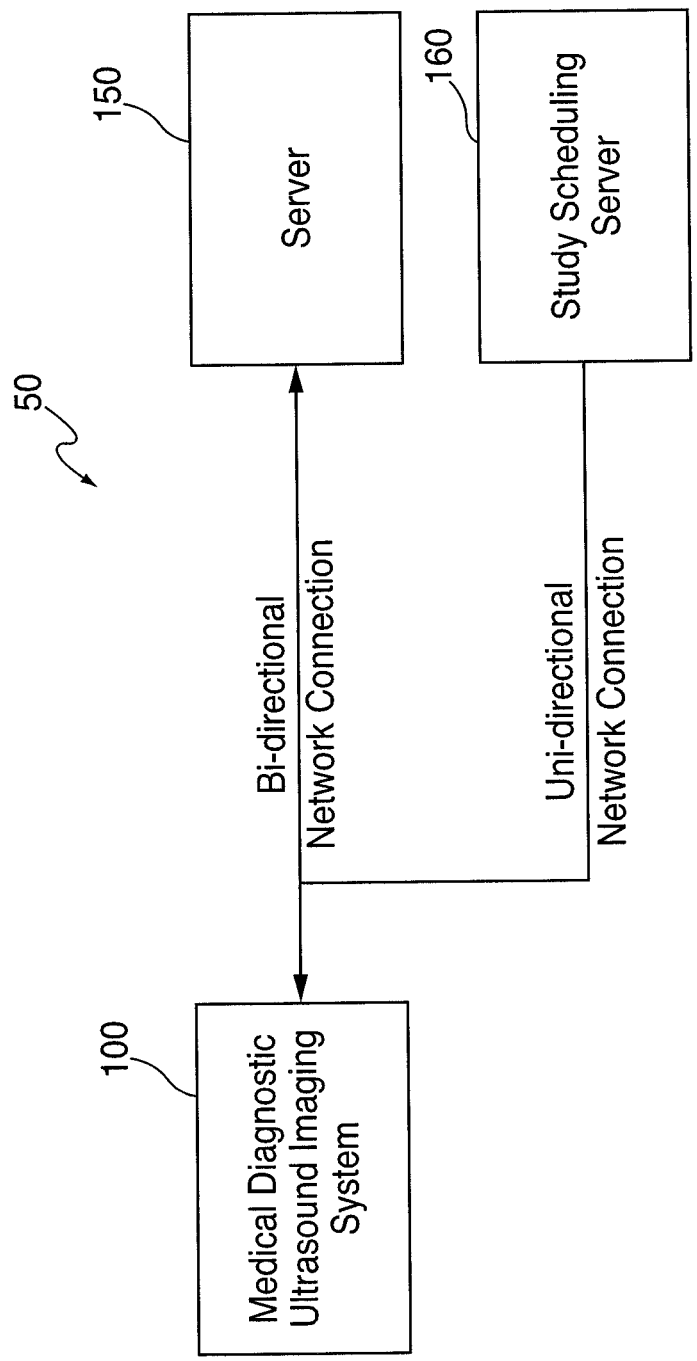
FIG. 1 is a block diagram of a network environment of an embodiment.

By way of introduction, the following embodiments provide a medical diagnostic ultrasound imaging system and method for receiving information from a server during an examination of a patient to improve workflow. While some prior medical diagnostic ultrasound imaging systems can communicate with a server during an examination, such communication is very limited and does not provide the interactivity that the following embodiments can provide to improve workflow. For example, some prior medical diagnostic ultrasound imaging systems can send captured ultrasound images to a server and can receive an acknowledgment back from the server that the images were received and stored. In contrast, in one embodiment, in response to receiving a captured image or other information about a patient, the server can return information to the medical diagnostic ultrasound imaging system that can improve the sonographer's workflow in conducting the examination. That is, these embodiments can provide a simplified workflow because the sonographer gets information that she otherwise would not get. Also, by having the server provide an intelligent, processed result, these embodiments can make the sonographer perform different acts during the examination of the patient.

For example, if the medical diagnostic ultrasound imaging system sends the server a measurement of anatomy under study, and the server can look-up previous measurement(s) of the anatomy, generate a plot showing the current and previous measurements, and send the plot to the medical diagnostic ultrasound imaging system for display to the sonographer. This can help the sonographer decide which images or measurements to take next. As another example, as a sonographer is filling-out a patient study worksheet on the medical diagnostic ultrasound imaging system, the information completed on the worksheet can be sent the server. The server can process the information to determine what remaining sections of the worksheet are relevant and only return the relevant remaining sections to the medical diagnostic ultrasound imaging system. This can improve the sonographer's workflow by eliminating the need for the sonographer to page through irrelevant sections of the worksheet and can also guide the sonographer in which images and measurements to take during the rest of the examination. As another example, the medical diagnostic ultrasound imaging system can provide the server with information about the patient, and, in response to this information, the server can provide the medical diagnostic ultrasound imaging system with images or reports from a prior study of the patient, which the sonographer may find useful in conducting a present examination of the patient. As yet another example, the sonographer can initiate on the ultrasound system an instant message to the radiology reading room asking whether it is OK to release the current patient. The server can send this message (e.g., encrypted) to the active workstations in the radiology reading room. In one embodiment, any physician can "click" on the message, whereupon the server would remove the message from all other workstations and open on the "clicked" workstation the in-progress ultrasound exam showing the sonographer's study worksheet, flagged images, and a window capable of showing all images acquired thus far. The physician can review the images and other information and send an instant message back to the ultrasound machine that the patient can be released or, alternatively, that additional images, tests, or other actions are needed. Of course, these are just examples, and other implementations can be used. Some of these possible implementations are discussed below.

Turning now to the drawings, FIG. 1 is a block diagram of a network environment 50 of an embodiment. As shown in FIG. 1, the network environment 50 of this embodiment comprises a medical diagnostic ultrasound imaging system 100 (sometimes referred to herein as the "ultrasound system"), a server 150 in bi-directional communication with the medical diagnostic ultrasound imaging system 100, and a study scheduling server 160 in uni-directional communication with the medical diagnostic ultrasound imaging system 100. As used herein, "in communication with" could mean directly in communication with or indirectly (wired or wireless) in communication with through one or more components, which may or may not be shown or described herein. Also, the terms "study" and "examination" (or "exam") will be used interchangeably herein.

As also used herein, the term "server" can mean a computer program or a device that provides functionality for other programs or devices ("clients"). Servers can provide various functionality ("services"), such as sharing data or resources among one or more clients or performing computation for one or more clients. A client can run on the same device as a server or may connect over a network to a server on a different device. Client-server systems can use a request-response communication technique in which a client sends a request to the server, and the server sends a response back to the client. In some embodiments, a server can be implemented as a physical server or a virtual server. Both can perform similar or identical functions, but their implementations can be different. For example, a physical server can be implemented using hardware (e.g., a CPU, memory, disk storage, network interface, etc), an operating system (e.g., Microsoft Windows Server 2012), and various software that may include, but is not limited to, drivers and application software. The term "physical server" can refer to the hardware, operating system, application, and other software. A virtual server can be implemented using hardware (e.g., a CPU, memory, disk storage, network interface, etc.), virtualizing software that acts to isolate the operating system from the hardware, an operating system, application, and other software. The term virtual server can refer to the operating system, application, and other software and exclude the hardware, or it can refer to both the software and the hardware. A virtual server may be located locally (e.g., in the medical institution's facilities) or "in the cloud" (e.g., when the virtual server is internet-based and provides shared processing resources and other on-demand services).

It should be noted that the network configuration 50 in FIG. 1 is merely one example, and other network configurations can be used. For example, in some embodiments, the study scheduling server 160 is not used or is in bi-directional communication with the medical diagnostic ultrasound imaging system 100. As another example, while FIG. 1 shows the communication between the medical diagnostic ultrasound imaging system 100, the server 150, and the study scheduling server 160 being over a network connection, in other embodiments, a network is not used (e.g., the medical diagnostic ultrasound imaging system 100 can be directly connected (not via a network) to the server 150 and/or the study scheduling server 160). Also, in another embodiment, the functionality of the server 150 and the study scheduling server 160 are combined into one device. It should also be understood that other devices (not shown) may be connected to the network and thereby be in bi-directional or uni-directional communication with the server 150. For example, various radiology workstations, radiology information systems (RIS), electronic medical record (EMR) systems, and PACS archives may be connected to the network.

Figure 2:
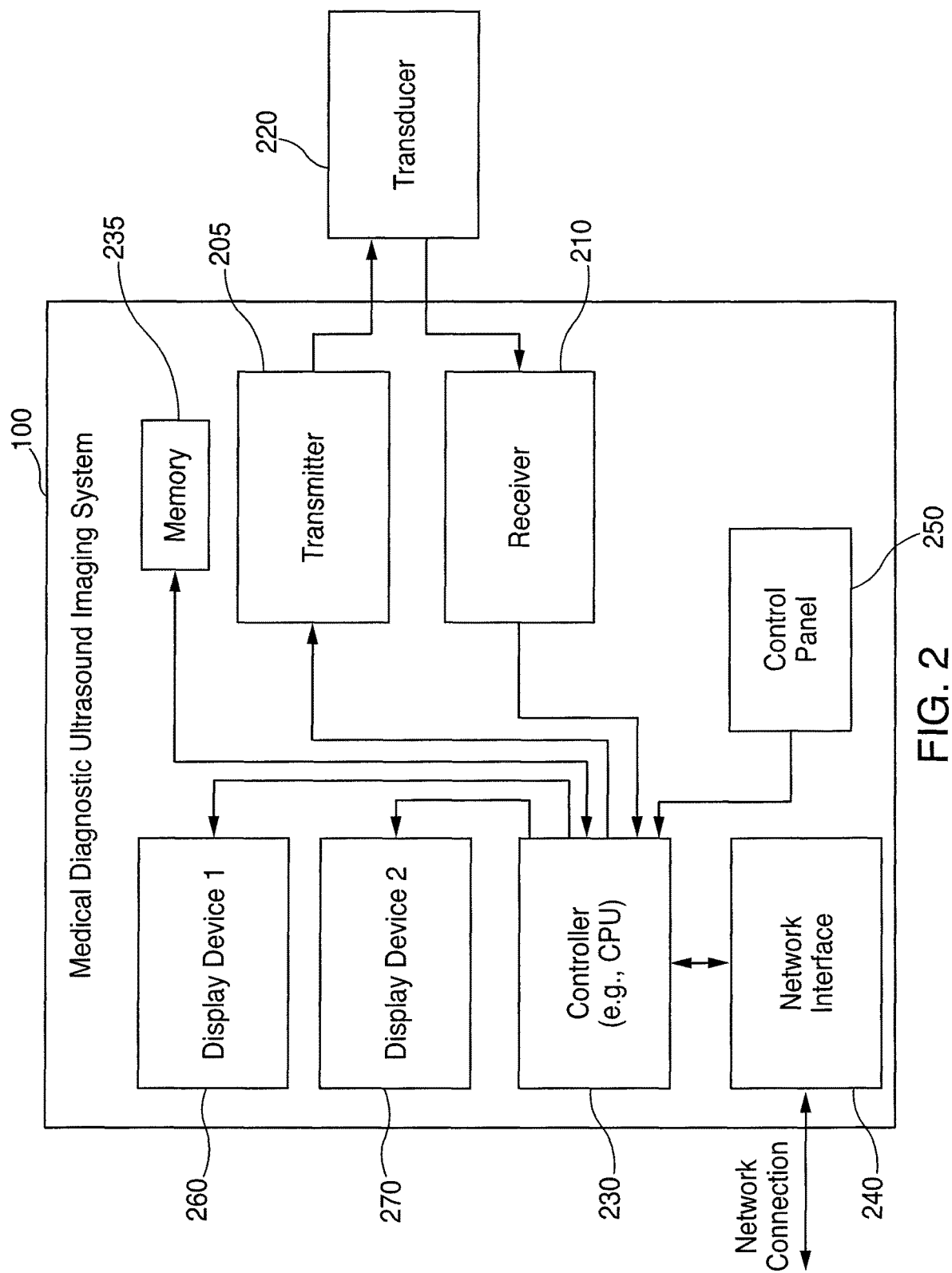
FIG. 2 is a block diagram of a medical diagnostic ultrasound imaging system of an embodiment.

FIG. 2 is a block diagram of a medical diagnostic ultrasound imaging system 100 of an embodiment. In this embodiment, the medical diagnostic ultrasound imaging system 100 comprises at least one transmitter 205 and at least one receiver 210 in communication with a transducer 220 and a controller 230. The medical diagnostic ultrasound imaging system 100 also comprises a memory (one or more volatile and/or non-volatile devices) 235, a network interface 240, a control panel 250, and first and second display devices 260, 270. It should be noted that this is merely one implementation, and other implementations can be used.

In this embodiment, the controller 230 is configured to control the operation of the medical diagnostic ultrasound imaging system 100. The controller 230 can take the form, for example, of processing circuitry, a microprocessor or processor, logic gates, switches, an application specific integrated circuit (ASIC), a field programmable gate array, a programmable logic controller, an embedded microcontroller, a digital circuit, an analog circuit, combinations thereof, and other now-known or later-developed devices for analyzing and processing data. The controller 230 can be configured with hardware and/or firmware to perform the various functions described below and shown in the flow diagrams. The controller 230 can also execute software to perform these and other functions. For example, the memory 235 (e.g., a computer-readable medium) can store computer-readable program code (e.g., software) executable by a (micro)processor in the controller 230. The software can include a set of instructions that may be executed to cause the controller 230 to perform any one or more of the methods or computer-based functions disclosed herein.

In this embodiment, the control panel 250 includes one or more user input devices, such as, but not limited to, a keyboard, a number pad, real or virtual knobs and buttons, a joystick, a mouse or other pointing/selecting device, a touch screen, a camera, a microphone, and a remote control device. One or both of the display devices 260, 270 can take the form of a liquid crystal display (LCD), an organic light emitting diode (OLED), a flat panel display, a solid state display, a cathode ray tube (CRT), a projector, or other now-known or later-developed display device technology for outputting information. In one embodiment, one display device 260 is a relatively-larger display device, and the other display device 270 is a relatively-smaller display device with a touch-sensitive display. Also, instead of two display devices, the medical diagnostic ultrasound imaging system 100 can have one display device or more than two display devices.

The network interface 240, which may be part of the controller 230, can be created in software and/or may be a physical connection in hardware. The network interface 240 may be configured to connect with a network and/or external media. The connection with the network may be a physical connection, such as a wired Ethernet connection, and/or may be established wirelessly, such as when a wireless network is used (e.g., a cellular telephone network or an 802.11, 802.16, 802.20, or WiMax network). The network can be a public network, such as the Internet, a private network, such as an intranet, or combinations thereof, and may utilize a variety of networking protocols now available or later developed including, but not limited to, TCP/IP-based networking protocols. In one embodiment, the medical diagnostic ultrasound imaging system 100 acts as a client to the server 150 in a client-server network environment. However, in other embodiments, the medical diagnostic ultrasound imaging system 100 and the server 150 are peer computer systems in a peer-to-peer (or distributed) network environment. In one embodiment, the medical diagnostic ultrasound imaging system 100 and the server 150 communicate using the Digital Imaging and Communications in Medicine (DICOM) standard.

The transducer 220 can comprise an array of piezoelectric materials, which can take the form of, for example, a phased linear, linear, curved linear, sector, wide view, single element, 1.5 dimensional, two dimensional, or other type of array of transducer elements. The transducer 220 is configured to convert a waveform from the transmitter 205 to acoustic energy and convert received acoustic energy to electrical signals, which are provided to the receiver 210. The transmitter 205 can comprise digital and/or analog devices for generating the waveform along one or more scan lines, and the receiver 210 can comprise digital and/or analog devices for processing the electrical signals representing echo signals received by the transducer along the one or more scan lines, after the acoustic energy is reflected off of anatomy in the patient. The transmitter 205 and/or receiver 210 can comprise discrete analog circuitry, including amplifiers, filters, digital-to-analog converters, and analog-to-digital converters, for example.

In general, during a medical diagnostic ultrasound examination of a patient, a sonographer contacts the transducer 220 with the patient, and the medical diagnostic ultrasound imaging system 100 acquires an ultrasound image in accordance with settings configured in the controller 230 (e.g., as inputted via the control panel 250). In general, the controller 230 causes the transmitter 205 to apply a voltage to the transducer 220 to cause it to vibrate and emit an ultrasonic beam into the portion of the patient's body in contact with the transducer 220. Ultrasonic energy reflected from the patient's body impinges on the transducer 220, and the resulting voltages created by the transducer 220 are received by the receiver 210. The controller 230 processes the sensed voltages to create an ultrasound image and can display the image on one or both of the display devices 260, 270. In addition to being displayed, the ultrasound image can be stored in digital form on the medical diagnostic ultrasound imaging system 100 and/or the network. For example, the sonographer can be given the option of storing an ultrasound image by pressing an "image capture" key on the control panel 250, or, alternatively, the ultrasound image can be automatically stored without user intervention. In this way, a series of images from an ultrasound exam can be stored for later review and analysis.

Figure 3:
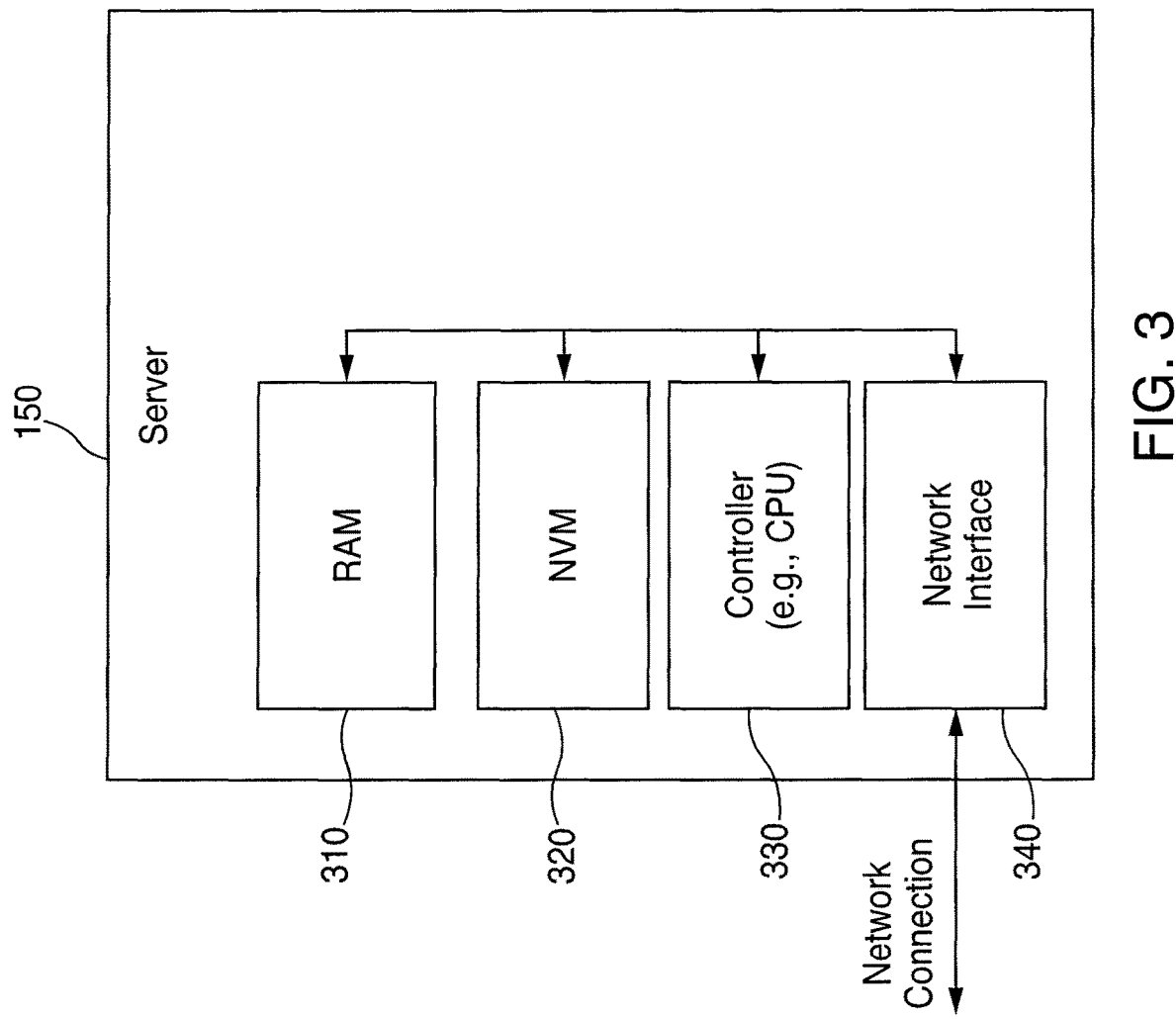
FIG. 3 is a block diagram of a server of an embodiment.

FIG. 3 is a block diagram of one implementation of the server 150 of an embodiment (other implementations can be used). As shown in FIG. 3, in this embodiment, the server 150 comprises RAM (or other volatile memory) 310, non-volatile memory 320 (e.g., solid state memory, a hard disk drive, an optical drive, etc.), a controller 330, and a network interface 340. The controller 330 and network interface 340 in the server 150 can take any suitable form, such as those described above with respect to the controller 230 and network interface 240, respectively, in the medical diagnostic ultrasound imaging system 100. However, the controller 330 and network interface 340 in the server 150 do not necessary need to be implemented in the same way as the controller 230 and network interface 240 in the medical diagnostic ultrasound imaging system 100. In this embodiment, the controller 330 in the server 150 is configured to implement the methods and algorithms discussed herein and shown in the accompanying flow charts to improve workflow in the medical diagnostic ultrasound imaging system 100.

Although not shown in the drawings, the study scheduling server 160 can be implemented in a similar way as the server 150. However, the controller in the study scheduling server 160 can be configured to provide study scheduling information to the medical diagnostic ultrasound imaging system 100. For example, the study scheduling server 160 can send a DICOM modality worklist to the medical diagnostic ultrasound imaging system 100 for display on the display device 260, 270. (While a worklist can be locally stored on the medical diagnostic ultrasound imaging system 100, having the study scheduling server 160 send a DICOM modality worklist to the medical diagnostic ultrasound imaging system 100 can provide department-wide uniformity.)

FIG. 4 is a screen shot of an exemplary DICOM modality worklist used to illustrate this embodiment. While a DICOM modality worklist is used in this example, it should be understood that other types of scheduled-patient lists or displays can be used. In general, a DICOM modality worklist is list of imaging procedures scheduled for the medical diagnostic ultrasound imaging system 100. As shown in FIG. 4, the DICOM modality worklist in this example includes patient name, patient medical number, reason for study, and study date and time. Other or different information can be displayed, such as, but not limited to, sex, age, the type of procedure, equipment type, procedure order, and referring physician. In operation, the sonographer selects the displayed line for the patient being examined and then presses a real or virtual "Start Study" button, which starts the ultrasound examination. These actions can be done using the control panel 250 (e.g., by using a mouse or cursor keys) or, if the display 260, 280 is touch-sensitive, but touching the displayed areas.

Figure 5:
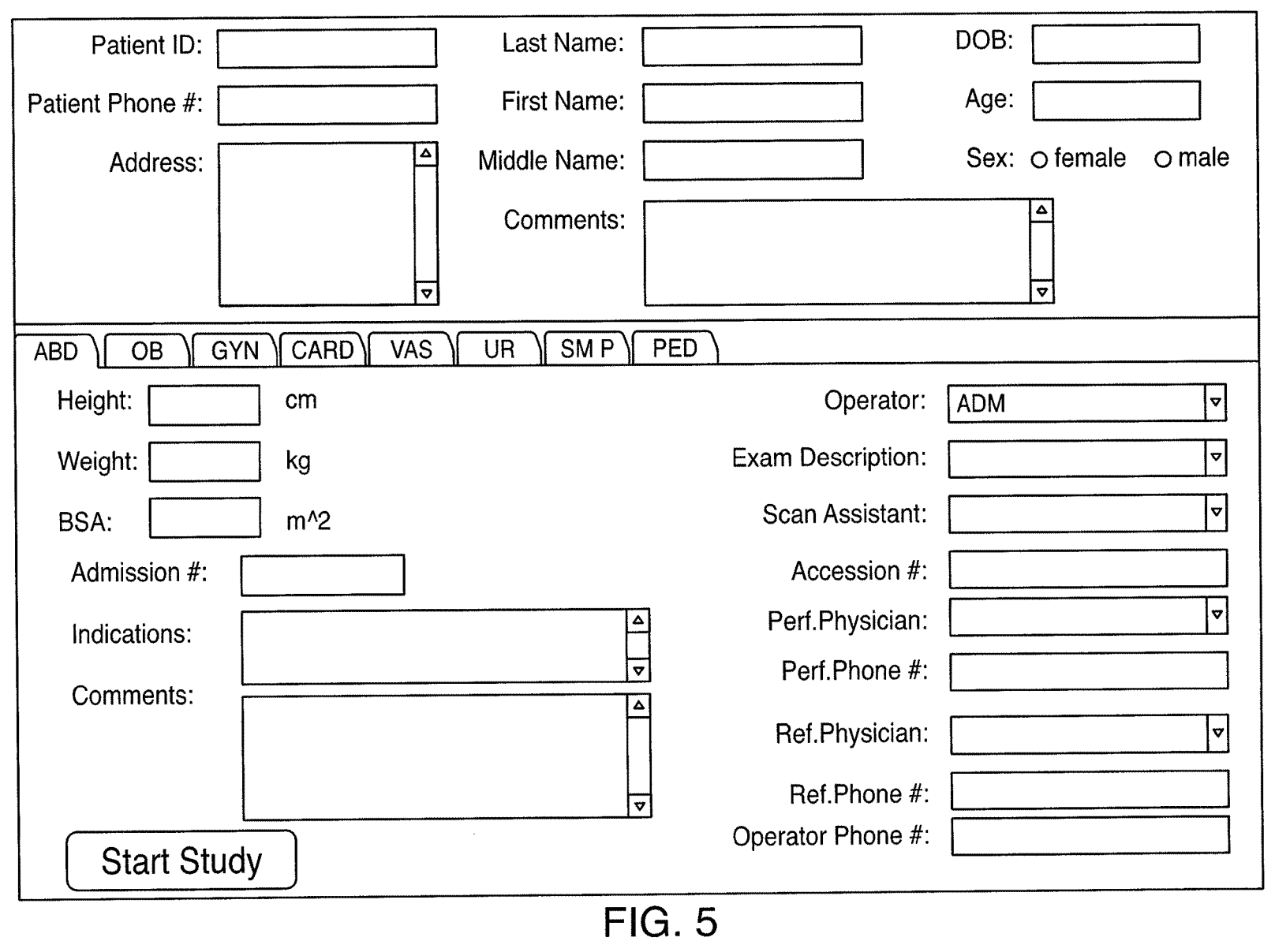

As an alternative to selecting a scheduled study from a DICOM modality worklist and then pressing the "Start Study" button, a sonographer can manually enter (e.g., using the control panel 250) information about a patient into a displayed form on the display device 260, 270. FIG. 5 is a screen shot of an exemplary patient input screen of an embodiment. As shown in FIG. 5, the sonographer can input information, such as patient ID and other patient-identifying information, as well as information about the examination. After the sonographer inputs the relevant information, the sonographer presses a real or virtual "Start Study" button, which starts the ultrasound examination.

Figure 6:
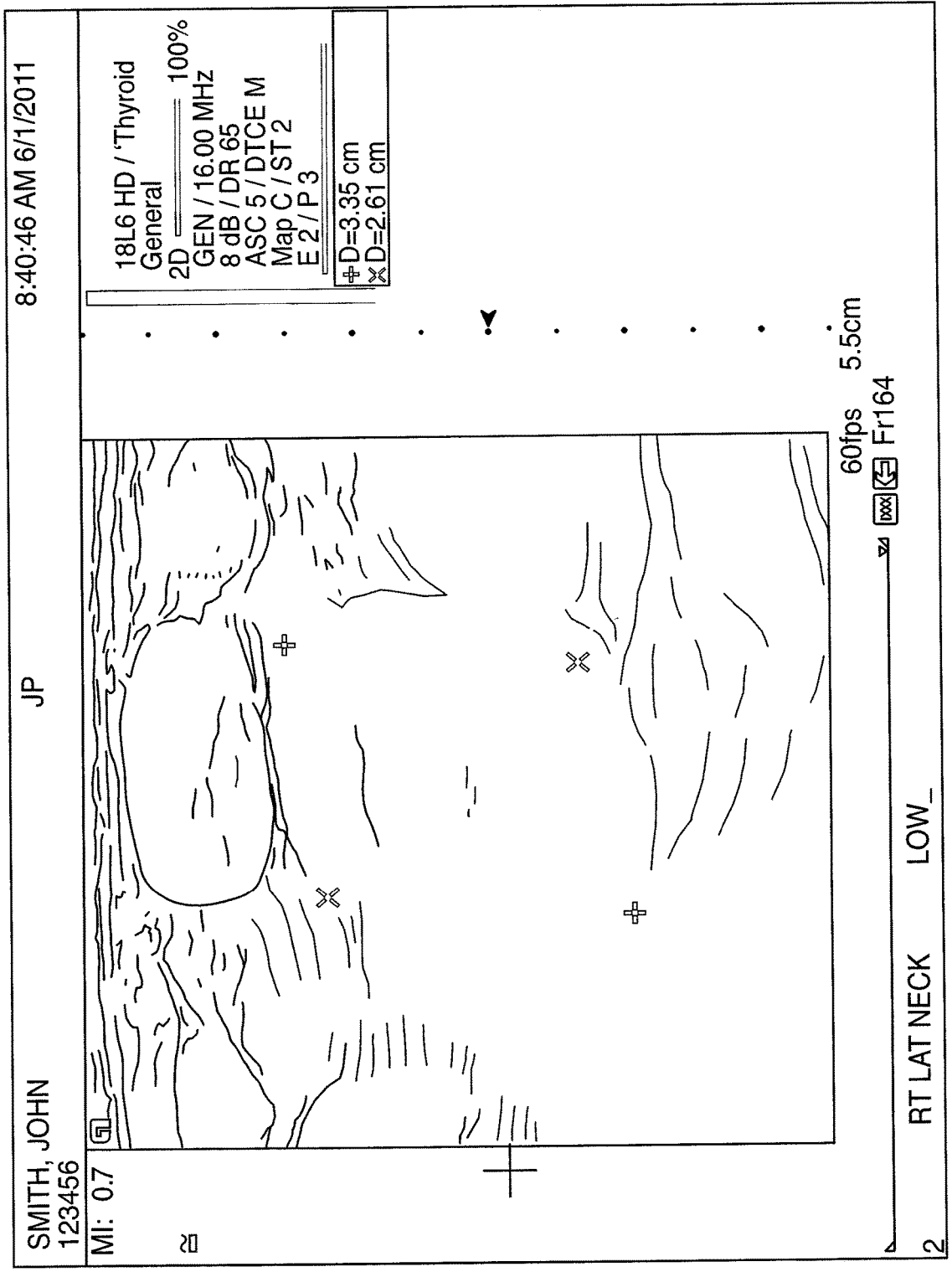
FIG. 6 is an illustration of an ultrasound image of an embodiment.

After the examination of the patient begins (e.g., after pressing the "Start Study" button on a DICOM modality worklist or a patient-input form), the sonographer conducts an ultrasound examination of the patient by contacting the transducer 220 to the patient and pressing a real or virtual "Capture" button on the medical diagnostic ultrasound imaging system 100 to generate ultrasound images (still images) or clips (i.e., a sequence of images that are played as a video (e.g., at 16 images/sec.)). FIG. 6 is an illustration of an example of an ultrasound image that can be displayed on the display device 260, 270 of the medical diagnostic ultrasound imaging system 100.

Figure 7:
FIG. 7 is an illustration of a patient worksheet of an embodiment.

During the examination, the sonographer can also enter observations (e.g., using the control panel 250) into a worksheet (e.g., a patient study worksheet) displayed on the medical diagnostic ultrasound imaging system 100. FIG. 7 is an example of a worksheet for an ultrasound examination of a thyroid. The sonographer can enter observations by pointing and clicking to select check boxes and radio buttons and entering text in text boxes.

After the sonographer captures all of the needed ultrasound images and completes the appropriate worksheet(s), the sonographer ends the examination by pressing a real or virtual "End Study" button. When the examination ends, the medical diagnostic ultrasound imaging system 100 can store the captured images, completed worksheet, and other information in the medical diagnostic ultrasound imaging system 100 and/or in the network (e.g., in the server 150) or in a storage location connected to the network such as a PACS archive.

During the time interval beginning when the "Start Study" button is pressed (or the equivalent) and when the "End Study" button is pressed (or the equivalent), the ultrasound exam may be described as "in progress." In one embodiment, the ultrasound machine is programmed to send in-progress captured images, measurements, and other information to the server immediately after these items are generated rather than waiting until the entire ultrasound exam is completed to send these items. When the ultrasound machine sends these data and various sonographer inputs to the server while the exam is in progress, the server can provide useful in-progress feedback to the ultrasound machine for use by the sonographer to improve workflow and facilitate the ultrasound study. In other embodiments, the ultrasound machine sends its information to the server after a "Pause Study" button, or the equivalent, is pressed, and the server returns information or other feedback to the ultrasound machine for the sonographer. In these embodiments, the sonographer may need to "Un-Pause," re-open, or re-start the study in order to perform additional measurements or additional imaging of the patient based on the feedback provided by the server. These other embodiments may provide a less-efficient workflow, but they may allow the ultrasound machine to "batch send" images and data rather than continuously send the images and data as they are acquired. For all of the above embodiments, the communication between the ultrasound machine and the server can be defined as occurring "during an examination" because the patient remains in the ultrasound exam room and the sonographer has the option of adding additional images, measurements, or other data to the patient's ultrasound exam.

Figure 8:
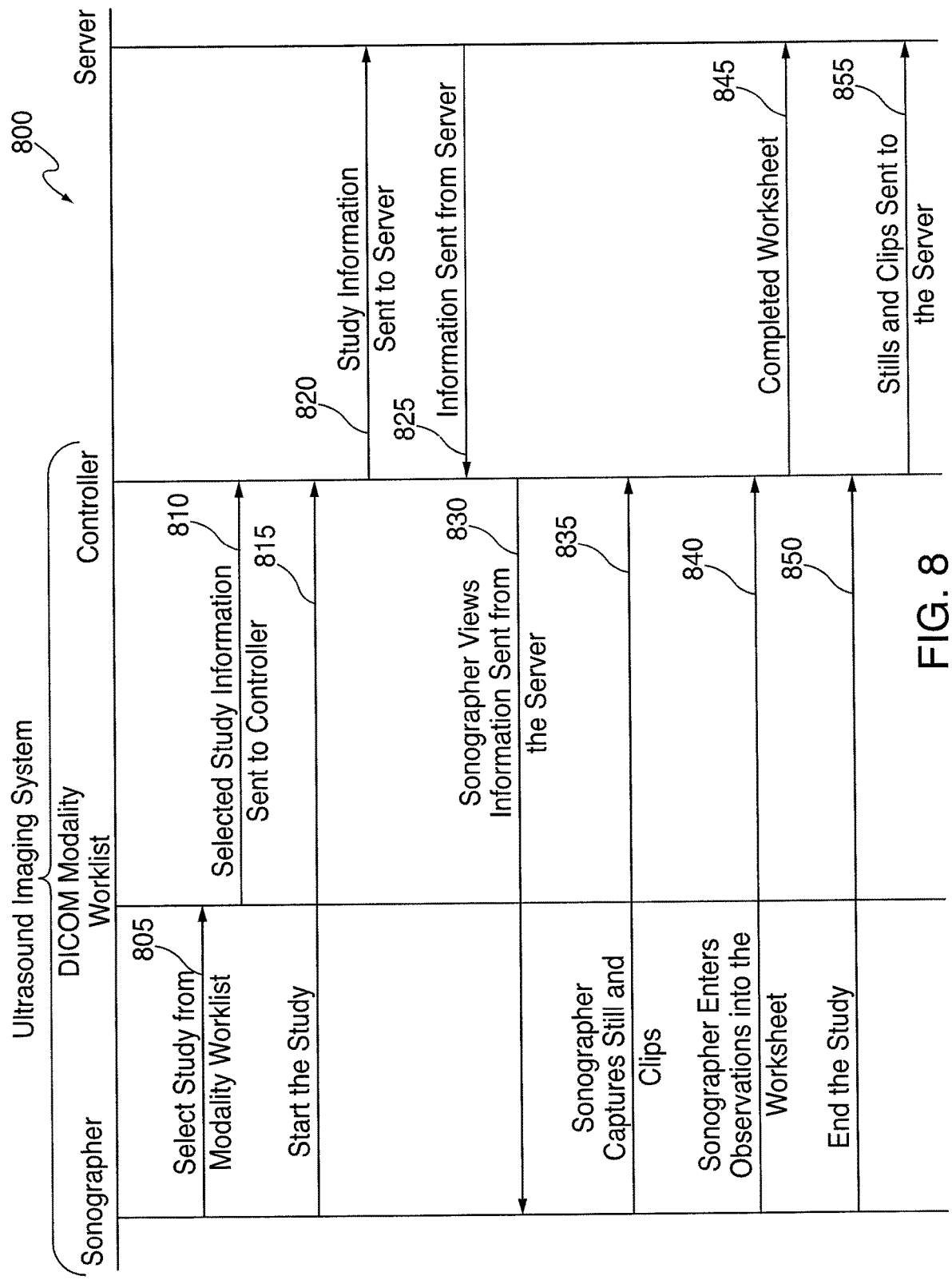
FIG. 8 is a flow diagram of communications between a medical diagnostic ultrasound imaging system and a server of an embodiment.

FIG. 8 is a flow diagram 800 of communication between the medical diagnostic ultrasound imaging system 100 and server 150. This is merely an example, and other flows are possible. Many of these acts are similar to those discussed above in conjunction with the normal operation of an ultrasound system (e.g., selecting a study from a modality worklist sent from a study scheduling server (act 805), sending the selected study information to the controller in the ultrasound system (act 810), starting the study/examination (act 815), capturing images (act 835), entering observations into a worksheet (act 840), and sending images to a server after the study has ended (acts 850 and 860).

While some prior medical diagnostic ultrasound imaging systems can communicate with a server during an examination, such communication is very limited. For example, some prior medical diagnostic ultrasound imaging systems can send captured ultrasound images to a server and can receive an acknowledgment back from the server that the images were received and stored. In contrast, the following embodiments provide a level of interactivity between the medical diagnostic ultrasound imaging system and the server that can improve workflow during the examination. More specifically, in this embodiment, the medical diagnostic ultrasound imaging system 100 sends first information about the patient to the server 150 (act 820). The first information can be sent in an encrypted or unencrypted ("in the clear") form. The "first information about the patient" can take any suitable form and can serve as a way for the server 150 to locate relevant information to send back to the medical diagnostic ultrasound imaging system 100 during the examination and/or can be processed by the server to provide a unique result to the medical diagnostic ultrasound imaging system 100. For example, the "first information about the patient" can be patient-identifying information, such as the patient's name or identifier, as selected from a DICOM modality worklist (see FIG. 4) or as inputted by a sonographer on a patient-input form (see FIG. 5). As another example, the "first information about the patient" can be something other than or in addition to information that merely identifies the patient. For example, "first information about the patient" can be a protocol step taken in a diagnostic procedure of a patient, information about the patient's study (e.g., a designation of the type of study being conducted on the patient (such as study type=abdomen or study type=leg), a unique study identifier for the patient's study, or accession number associated with the patient), or information about the patient that is generated during the examination of the patient (e.g., a captured image or measurement of an anatomy of the patient). The term "patient information" will be used herein to refer to any information about the patient, including information identifying the patient and information derived from an examination of the patient.

While patient identifier and/or a study identifier will be used in this example to illustrate these embodiments, it should be noted that other forms of "first information the patient" can be used. For example, the first information sent to the server 150 comprises information entered into a patient worksheet, which can be found locally on the medical diagnostic ultrasound imaging system 100 or sent from the server 150 (e.g., the server 150 can select which patient worksheet to send to the medical diagnostic ultrasound imaging system 100 based on the patient identifier and/or study identifier). The information entered into the patient worksheet can take any form, including, but not limited to, a keystroke input, a mouse click input, a selection of a cursor location, a selection of a touch screen location, a measured value, a calculated value, an identification of a value, information about the examination, and information about a protocol step in a diagnostic procedure. As another example, the first information about the patient sent to the server 150 includes one or more of the following: a medical diagnostic ultrasound image, a reference to a medical diagnostic ultrasound image, an "instant message" created by the sonographer, and a sequence of medical diagnostic ultrasound images. As shown from these examples, "first information about the patient" can be information that is derived from the current examination of the patient. Examples of information that is derived from an examination of a patient include, but are not limited to, a medical diagnostic ultrasound image of the patient, a reference to a medical diagnostic ultrasound image of the patient, a sequence (a "clip") of medical diagnostic ultrasound images of the patient, and a measurement, observation, or finding entered into a worksheet on the medical diagnostic ultrasound imaging system. Of course, these are merely examples, and other information about the patient can be sent to the server 150.

The first information can be sent to the server 150 before or after the examination begins or at the exact moment the examination begins. For example, when the first information about the patient is a patient identifier and/or a study identifier obtained from a DICOM modality worklist, the first information about the patient can be send before or after the "Start Study" button is pressed, or simultaneously when the "Start Study" button is pressed. Also, as will be discussed in more detail below, "first information" is not necessarily the first data transmission from the medical diagnostic ultrasound imaging system 100 and the server 150. Further, there can be multiple instances of "first information" sent from the medical diagnostic ultrasound imaging system 100 to the server 150 (and multiple instances of "second information" returned from the server 150 in response) during an examination to provide multiple instances of interactivity.

When the server 150 receives the first information about the patient from the medical diagnostic ultrasound imaging system 100, the controller 330 in the server 150 uses the first information to locate or generate "second information" about the patient. For example, the non-volatile memory 320 of the server 150 can store various information about patients in a database or other data structure, and the controller 330 in the server 150 can query the database with the first information about the patient (e.g., the patient identifier and/or study identifier) to locate the relevant second information about the patient. Instead of being stored in the non-volatile memory 320 of the server 150, the second information can be stored in an external storage location, such as an electronic medical record (EMR) system or archive and a picture archive and communication system (PACS) archive. Accordingly, the second information can be accessed by the server 150 from a local or external storage location. As another example, if the first information is a measurement of an anatomy of the patient, the server 150 can process the information to return a chart of current and previous measurements of the anatomy. As yet another example, if the first information is information entered into a patient study worksheet, the server 150 can process the entered worksheet information to generate information customized for the specific protocol being used to guide the sonographer to perform certain steps.

Referring back to FIG. 8, after the server 150 locates or generates the second information about the patient based on the first information about the patient, the server 150 sends the second information to the medical diagnostic ultrasound imaging system 100 (act 825). As with the first information, the second information can be sent in an encrypted or unencrypted ("in the clear") form. Also, the first and second information can both be encrypted or both be unencrypted, or one of the first and second information can be encrypted, while the other of the first and second information can be unencrypted. This information can be sent in any suitable way. For example, in one embodiment, the server 150 streams the second information to the medical diagnostic ultrasound imaging system 100. As used herein, "streaming" refers to the process that allows part of a file to be displayed after is it received, instead of having to wait for the entire file to be downloaded before any part of the file can be displayed.

It should be noted that while FIG. 1 shows a bi-directional connection between the medical diagnostic ultrasound imaging system 100 and the server 150, there can by bi-directional communication or uni-directional communication during an examination. For example, if the first information about the patient is sent to the server 150 during the examination and the second information about the patient is received from the server 150 during the examination, there would be bi-directional communication during the examination. However, if the first information about the patient is sent to the server 150 before the start of the examination, there may only be uni-directional communication during the examination, with the server 150 sending the second information about the patient. That being said, bi-directional communication during the examination allows multiple instances of interactivity during the examination that may be useful in certain situations to improve workflow.

Figure 13:
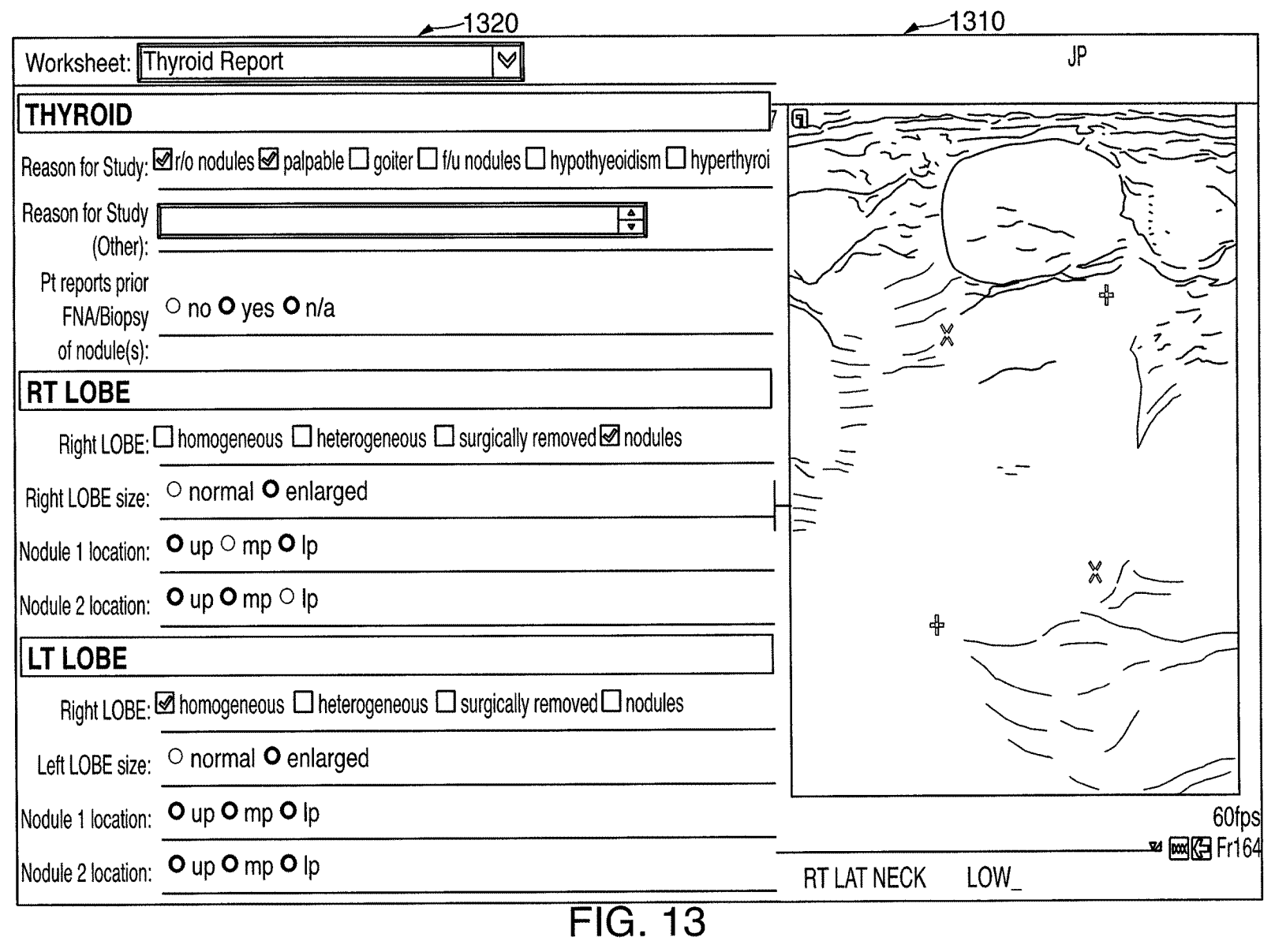
Figure 14:
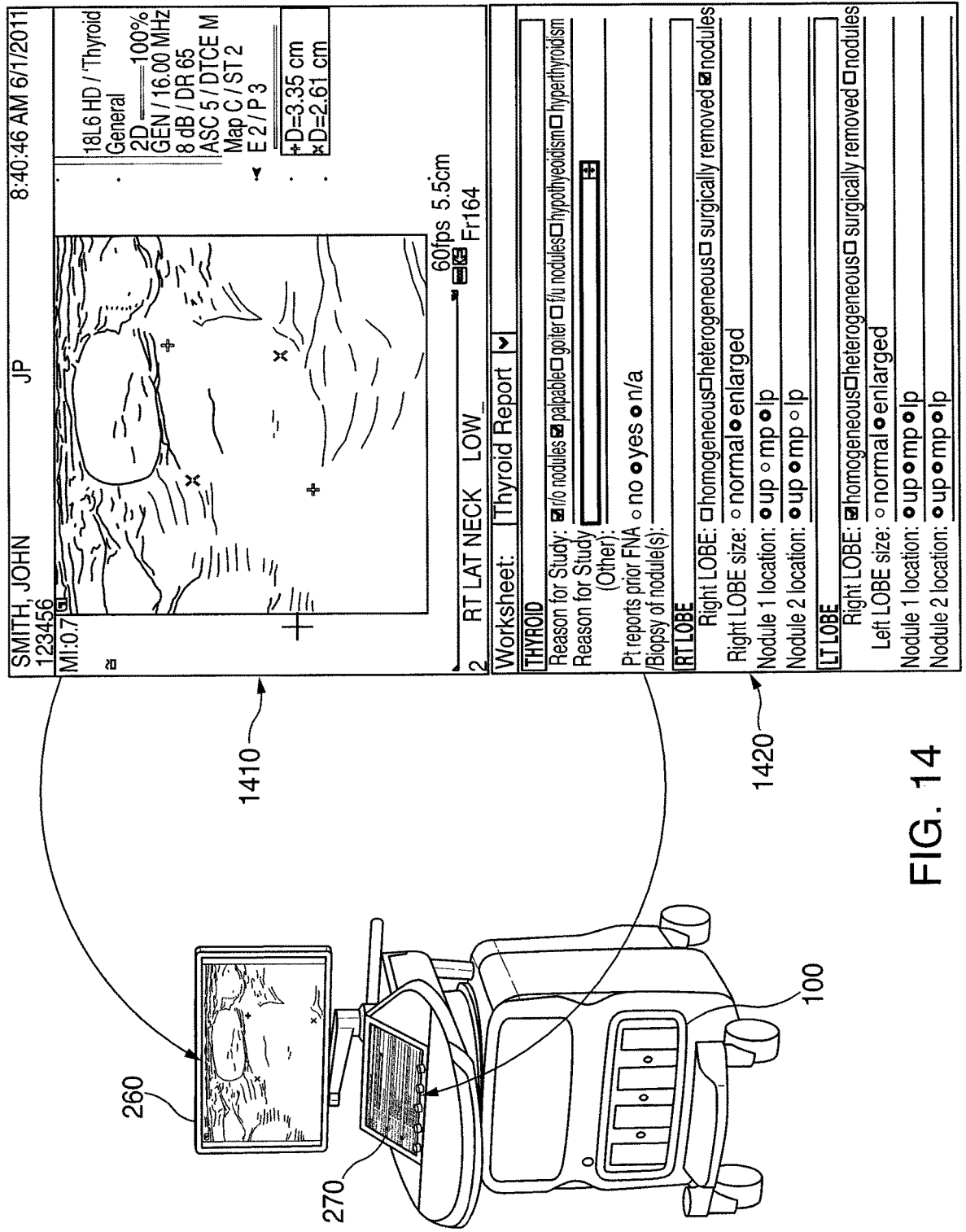
FIG. 14 is an illustration of a medical diagnostic ultrasound imaging system of an embodiment in which an ultrasound image and a patient worksheet are simultaneously displayed on two separate display devices.

After the medical diagnostic ultrasound imaging system 100 receives the second information about the patient from the server 150, the sonographer can view the second information on one or both of the display devices 260, 270 of the medical diagnostic ultrasound imaging system 100 (act 830). If the medical diagnostic ultrasound imaging system 100 has more than two display devices, the second information can be displayed on the additional display devices as well. For example, the second information about the patient received from the server 150 can be simultaneously displayed (e.g., on one or more display devices) with a medical diagnostic ultrasound image generated by the medical diagnostic ultrasound imaging system 100. For example, as shown in FIG. 13, an ultrasound image (e.g., from a current study) 1310 can be simultaneously displayed with a patient worksheet 1320 on one of the display devices 260, 270 of the medical diagnostic ultrasound imaging system 100. Alternatively, as shown in FIG. 14, the ultrasound image 1410 and the patient worksheet 1420 can be displayed simultaneously, with the ultrasound image 1410 being displayed on the first display device 260 at the same time the patient worksheet 1420 is displayed on the second display device 270.

The "second information about the patient" can take any suitable form. In one embodiment, the "second information about the patient" is information for use by a sonographer during the examination of the patient. Examples of "second information about the patient" include, but are not limited to, an automatically-selected medical diagnostic ultrasound image of the patient from a prior examination, a drawing made during a prior examination, a prompt to acquire an additional medical diagnostic ultrasound image of the patient, an instant message from a radiologist, a processed image from a current examination of the patient (e.g., such as when artificial intelligence is used to identify and grade a lesion or perform another type of analysis), information from the patient's medical record, the name of the doctor who ordered a prior study, the reason for the prior study, a reading physician's report to the referring physician of the prior study, measured values from the prior study, and trended values of the prior study. As another example, the second information about the patient can be a patient study worksheet tailored to the patient. For example, as a sonographer is filling-out a patient study worksheet on the medical diagnostic ultrasound imaging system, the information completed on the worksheet (the "first information") can be sent to the server 150. The server 150 can process the first information to determine what remaining sections of the worksheet are relevant and only return the relevant remaining sections (the "second information") to the medical diagnostic ultrasound imaging system 100. Of course, these are just examples, and other information can be provided.

It should be noted that, in some embodiments, the "second information about the patient" is sent after the server 150 sends an acknowledgement of receipt of the "first information about the patient" or some other transmission further to a communications protocol. That is, in some embodiments, the "second information about the patient" is information identified by or generated from the "first information about the patient" and excludes ancillary communication protocol transmissions.

The following paragraphs provide examples of different types of "second information about a patient" received from the server 150. It should be noted that these are merely examples and that other implementations can be used.

Figure 9:
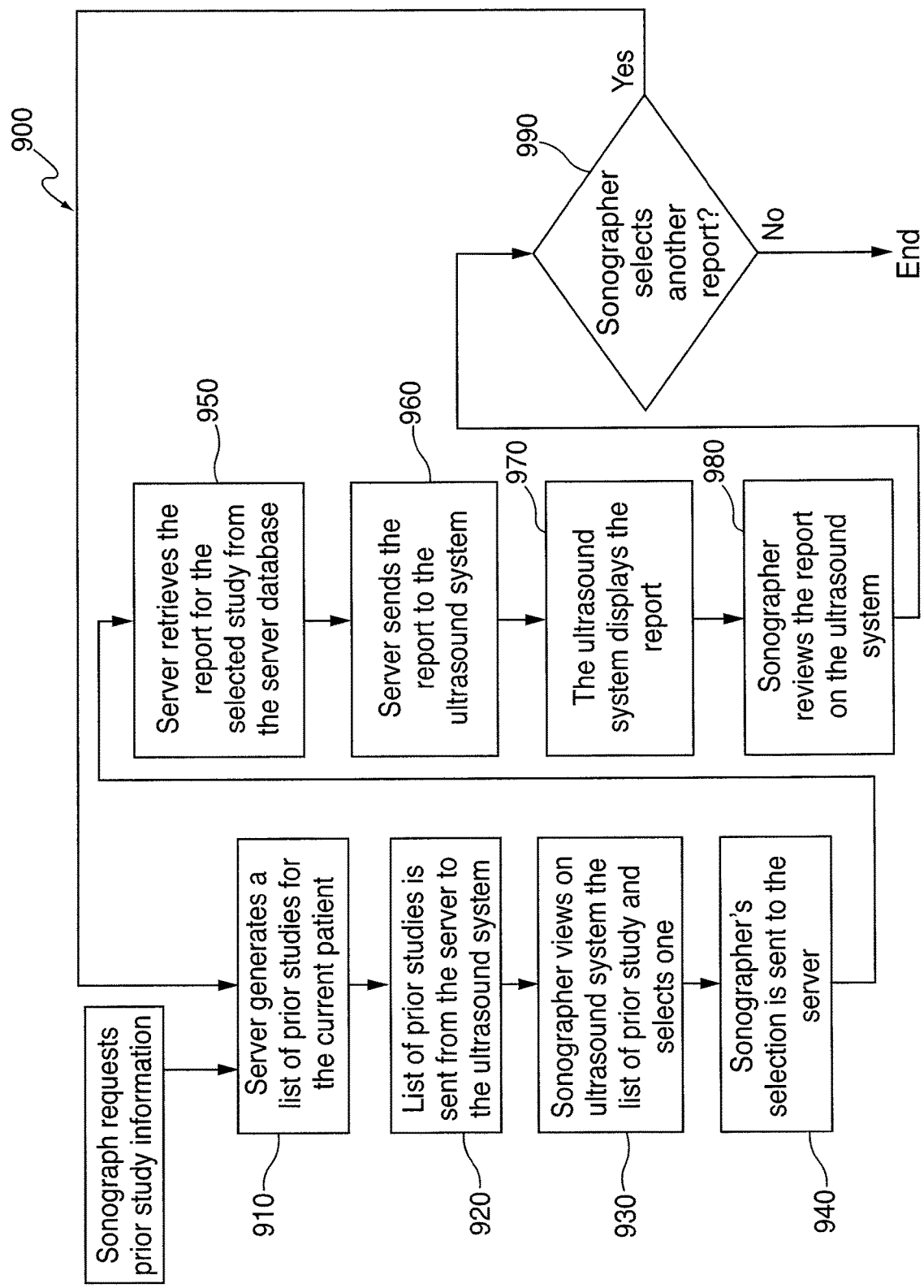
FIG. 9 is a flow chart of a method of an embodiment for displaying a report of a prior study sent from a server to a medical diagnostic ultrasound imaging system during an examination of a patient.

Returning to the drawings, FIG. 9 is a flow chart 900 that illustrates a situation in which the "second information about a patient" received from the server is a report of a prior study. A prior study can be useful to the sonographer in conducting the current examination, as it can suggest to the sonographer what images and/or measurements to take. As shown in FIG. 9, in response to the server 150 receiving the first information about the patient from the medical diagnostic ultrasound imaging system 100, the server 150 generates a list of prior studies for the current patient (act 910) and sends the list to the medical diagnostic ultrasound imaging system 100 (act 920). The sonographer then views the list of prior studies on one of the displays 260, 270 and selects a desired study and function button (act 930). The selection is then sent to the server 150 (act 940).

FIG. 10 is an example of a screen shot of prior study list sent from the server 150 and displayed on the medical diagnostic ultrasound imaging system 100. As shown in FIG. 10, in this example, the prior study list for this patient include two prior studies, identified by date, accession number, indication, and referring physician. The sonographer can select a desired study by using the control panel 250 (e.g., a mouse or keyboard). In this example, the sonographer has five options to view information from a selected study: Order, Report, Images, Measured Values, and Trended Values. The sonographer can select one of these options by clicking on the desired displayed button. Selecting the order button will result in the display of information about the order for the selected prior study (e.g., the name of the doctor who ordered the study and the reason for the study). Selecting the report button will result in the display of a report generated for the study (e.g., the reading physician's report to the referring physician). Selecting the images button will result in the display of ultrasound images from the selected prior study. Selecting the measured values button will result in the display of values measured for the selected study (e.g., for a thyroid study, the length of a thyroid nodule). Selecting the trended values button will result in the display of a plot of measured values over time (e.g., for a thyroid study, a plot of the length of the nodule over time).

In this example, the selected function was "Report," so the server 150 retrieves the report for the selected study from the server's database (e.g., stored in RAM 310 or non-volatile memory 320) (act 950). The server 150 then sends the report to the medical diagnostic ultrasound imaging system 100 (act 960), and the medical diagnostic ultrasound imaging system 100 displays the report (act 970). The sonographer then can review the report on the medical diagnostic ultrasound imaging system 100 (act 980) and select another report, if desired (act 990). Flows similar to the one shown in FIG. 9 would take place if the sonographer presses the Order, Images, Measured Values, or Trended Values buttons.

Figure 11:
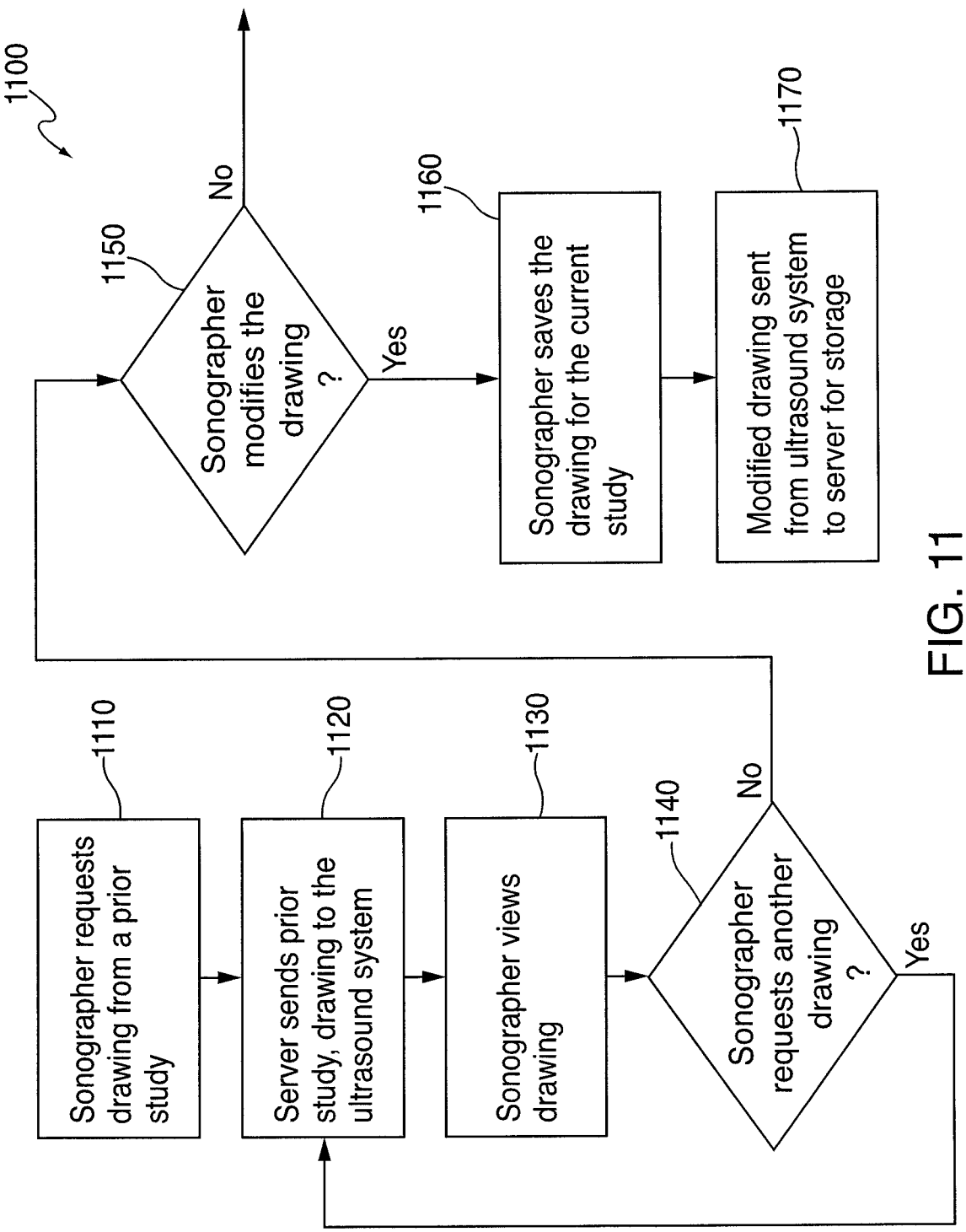
FIG. 11 is a flow chart of a method of an embodiment for displaying a drawing of a prior study sent from a server to a medical diagnostic ultrasound imaging system during an examination of a patient.

It should be noted that the buttons shown on the screen shot in FIG. 10 are just examples, and other buttons can be used. For example, in another embodiment, the sonographer has the option of pushing a Drawing button. A flow chart 1100 illustrating this method is presented in FIG. 11. As shown in FIG. 11, when the sonographer clicks on the Drawing button (act 1110), a signal is sent to the server 150, and the server 150 sends a drawing from a prior study to the medical diagnostic ultrasound imaging system 100 (act 1120). The sonographer can then view the drawing from the selected prior study on the display 260, 270 of the medical diagnostic ultrasound imaging system 100 (act 1120). The drawing from the prior study can be a sketch the prior sonographer or reading physician made of some anatomy of the patient (e.g., the shape of a tumor or the approximate location of a tumor within an organ). There can be several prior drawings made, and the sonographer has the option of requesting additional drawings, if needed (act 1140). If the sonographer sees a change in the anatomy with respect to what is shown in the drawing from the prior study, the sonographer can create a modified version of the drawing (e.g., showing the new shape of the anatomy). In such a situation (act 1150), the sonographer can save the new drawing for the current study locally on the medical diagnostic ultrasound imaging system 100 (act 1160). The new drawing can also be sent from medical diagnostic ultrasound imaging system 100 to the server 150 for storage (act 1170).

Figure 12:
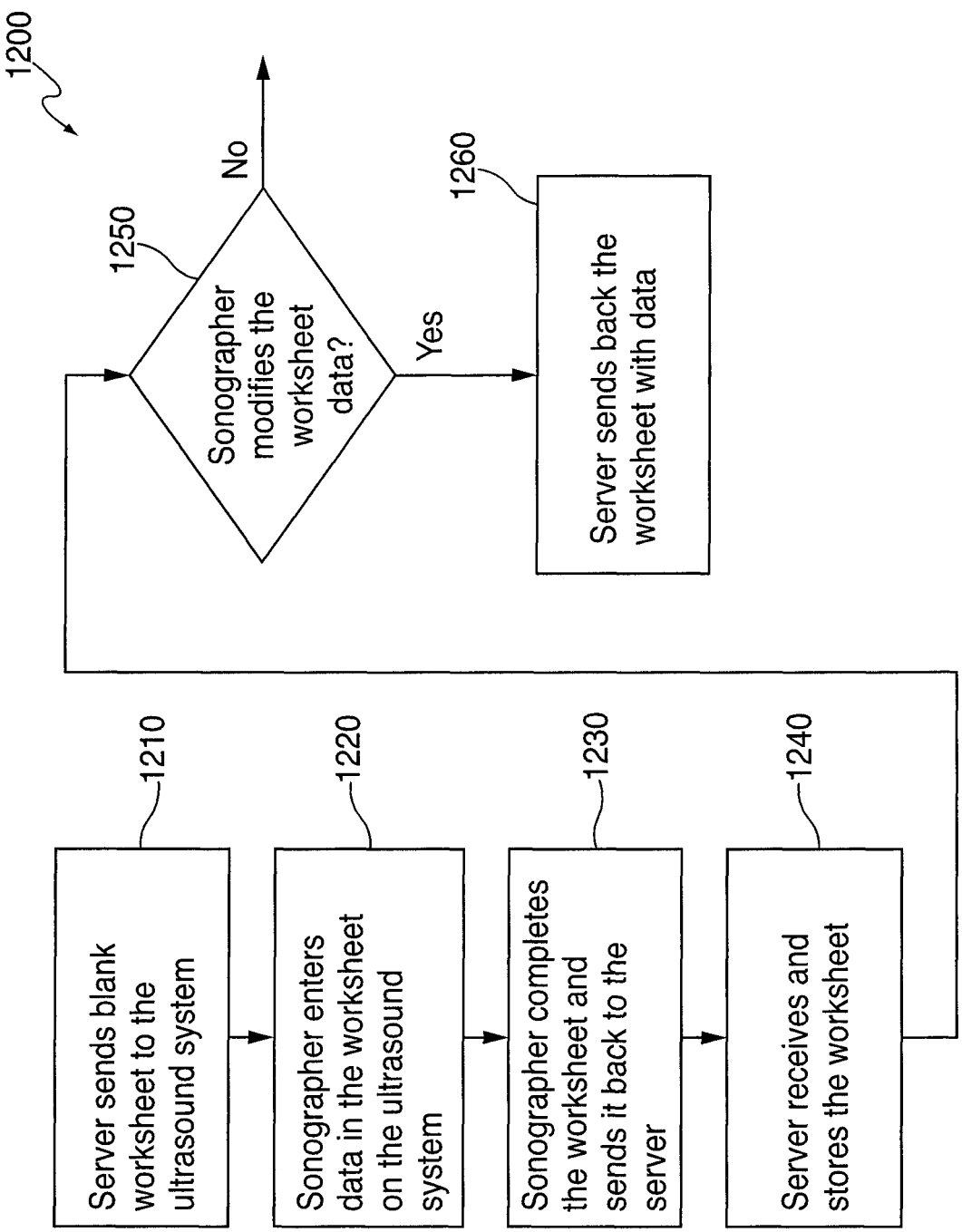
FIG. 12 is a flow chart of a method of an embodiment for displaying a patient worksheet sent from a server to a medical diagnostic ultrasound imaging system during an examination of a patient.

In addition to providing information about prior data about the patient, the server 150 can provide the medical diagnostic ultrasound imaging system 100 with the patient worksheet based on the first information about the patient sent to the server 150. This example will now be illustrated in conjunction with the flow chart 1200 in FIG. 12. As shown in FIG. 12, in response to receiving first information about the patient from the medical diagnostic ultrasound imaging system 100, the server 150 sends a blank patient worksheet (such as the one shown in FIG. 7) to the medical diagnostic ultrasound imaging system 100 (act 1210). The sonographer can then enter data into the worksheet using the control panel 250 of the medical diagnostic ultrasound imaging system 100 (act 1220). For example, the information entered into the patient worksheet can comprise one or more of the following: a keystroke input, a mouse click input, a selection of a cursor location, a selection of a touch screen location, a measured value, a calculated value, an identification of a value, information about the examination, and information about a protocol step in a diagnostic procedure. After the sonographer completes the worksheet, it is sent back to the server 150 (act 1230), which stores the worksheet in its memory (act 1240). If the sonographer later wants to modify the worksheet data (act 1250), the server 150 can send the stored worksheet (with previously-entered data) back to the medical diagnostic ultrasound imaging system 100 (acts 855 (FIG. 8) and 1260 (FIG. 12)). While FIG. 8 shows the completed worksheet sent to the server 150 before the end of the study, in other embodiments, the completed worksheet can be sent after the end of the study. Also, while FIG. 8 shows the ultrasound images sent to the server after the end of the study, in other embodiments, the ultrasound images can be sent before the end of the study.

Figure 15:
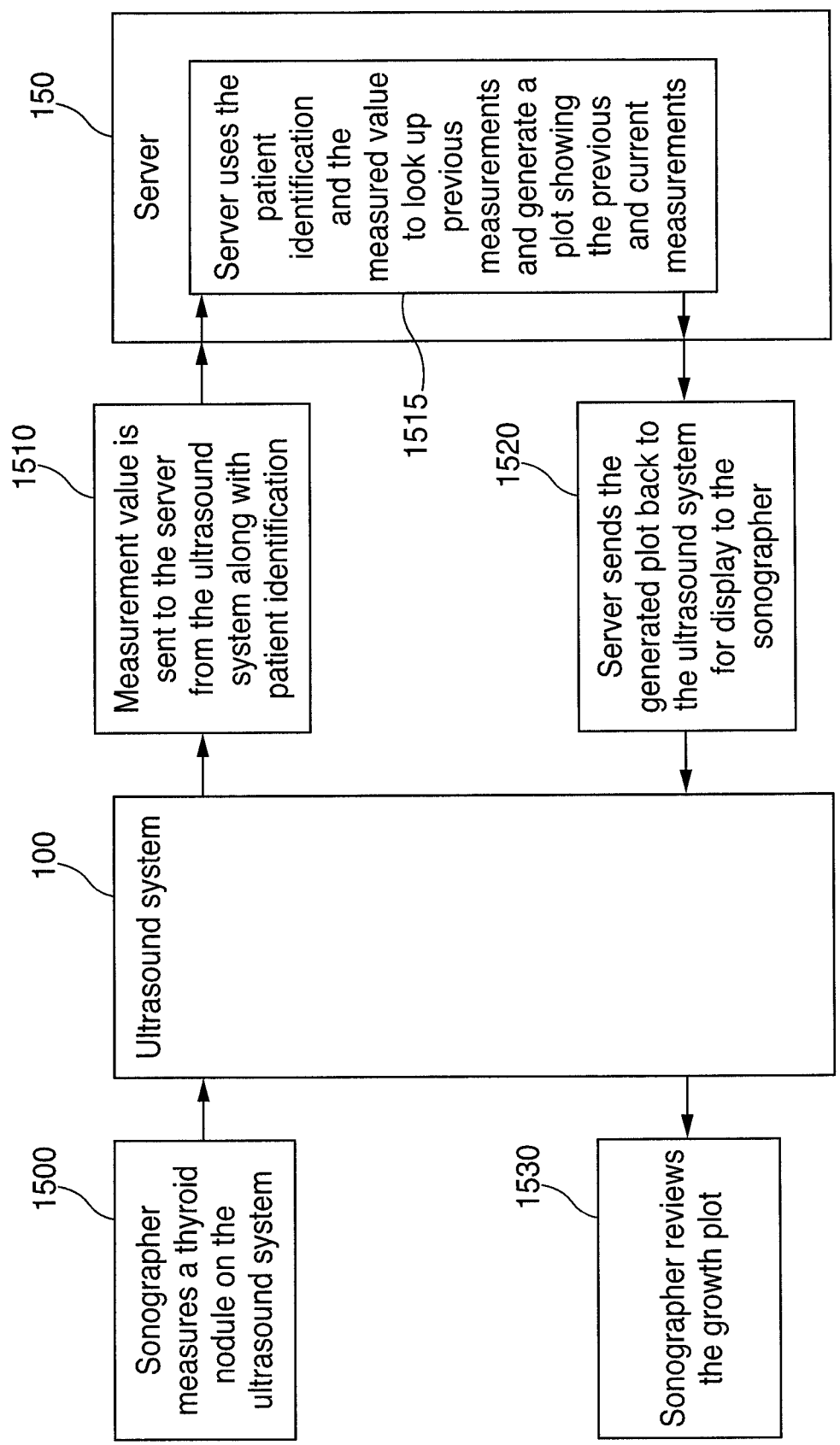
FIG. 15 is an illustration of an embodiment in which a server automatically generates a plot of current and previous measurements.
Figure 16:
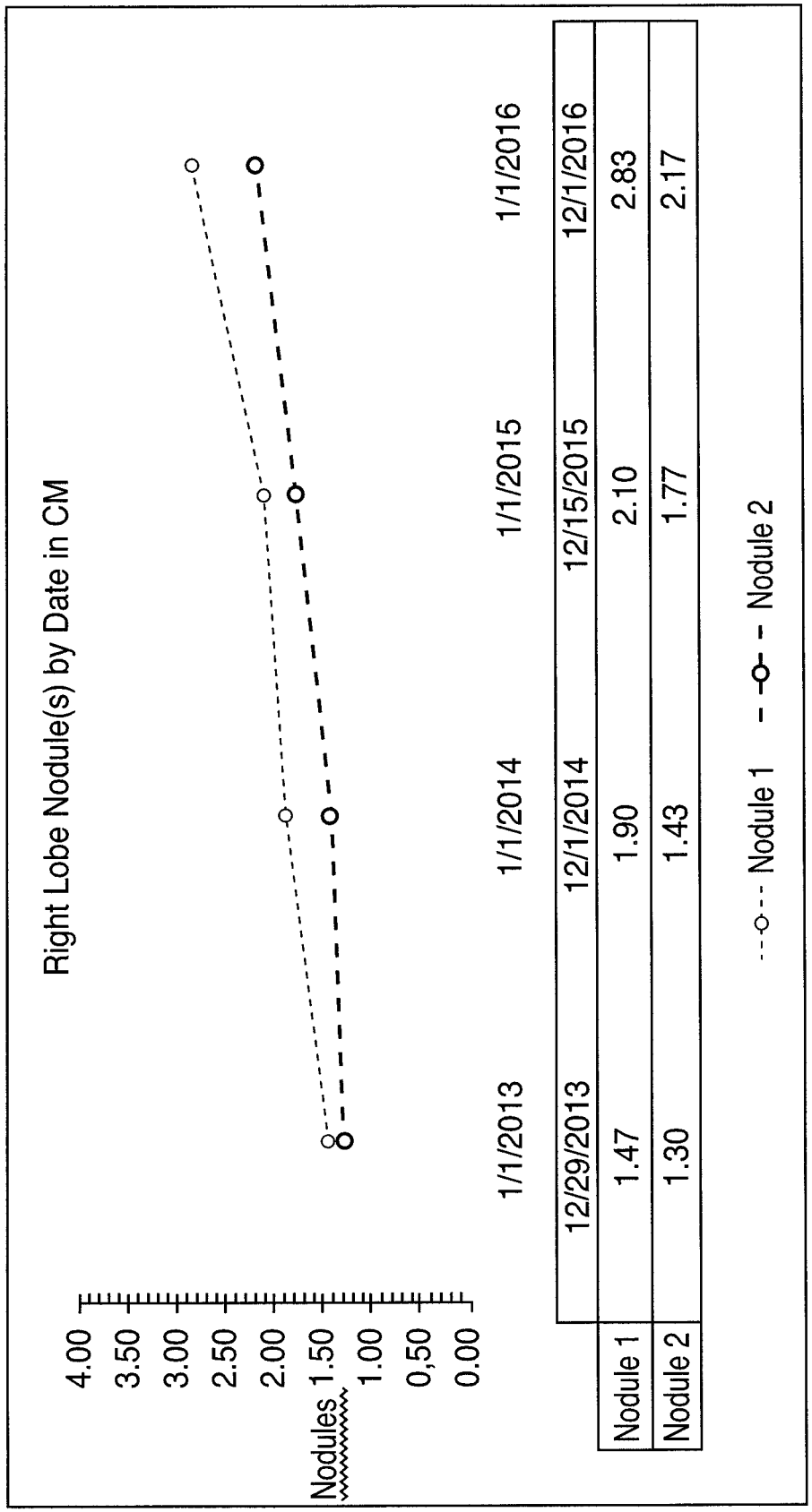
FIG. 16 is an illustration of a plot generated by a server of an embodiment of current and previous measurements.

While some of the above examples show the server 150 using the first information to look-up stored second information, as noted above, the server 150 can additionally or alternatively process the first information to generate the second information (e.g., the server 150 can provide information that is "unique," in that it is not previously stored in either the medical diagnostic ultrasound imaging system 100 or the server 150). For example, if the medical diagnostic ultrasound imaging system 100 sends the server 150 a measurement of anatomy under study, and the server 150 can look-up previous measurement(s) of the anatomy, generate a plot showing the current and previous measurements, and send the plot to the medical diagnostic ultrasound imaging system 100 for display to the sonographer. By generating a plot that did not exist before, the server 150 is doing something more than just looking up and returning stored data. That is, the server 150 responds to information about the patient (here, information that is provided by the sonographer and was derived during the current examination of the patient) by processing the information and sending back new information to the ultrasound system 100. This example is illustrated in FIGS. 15 and 16. In FIG. 15, the sonographer measures a thyroid nodule of a patient on the medical diagnostic ultrasound imaging system 100 (act 1500). The measurement value, along with the patient identification, is sent to the server 150 (act 1510). The server 150 uses the patient identification and the measured value to look-up previous measurements of the patient's thyroid and automatically generates a plot (see FIG. 16) showing the previous and current measurements (act 1515). The server 150 then sends the generated plot back to the medical diagnostic ultrasound imaging system 100 for display to the sonographer (act 1520). The sonographer can then review the growth plot (act 1530), which can assist the sonographer in the current study.

Figure 17:
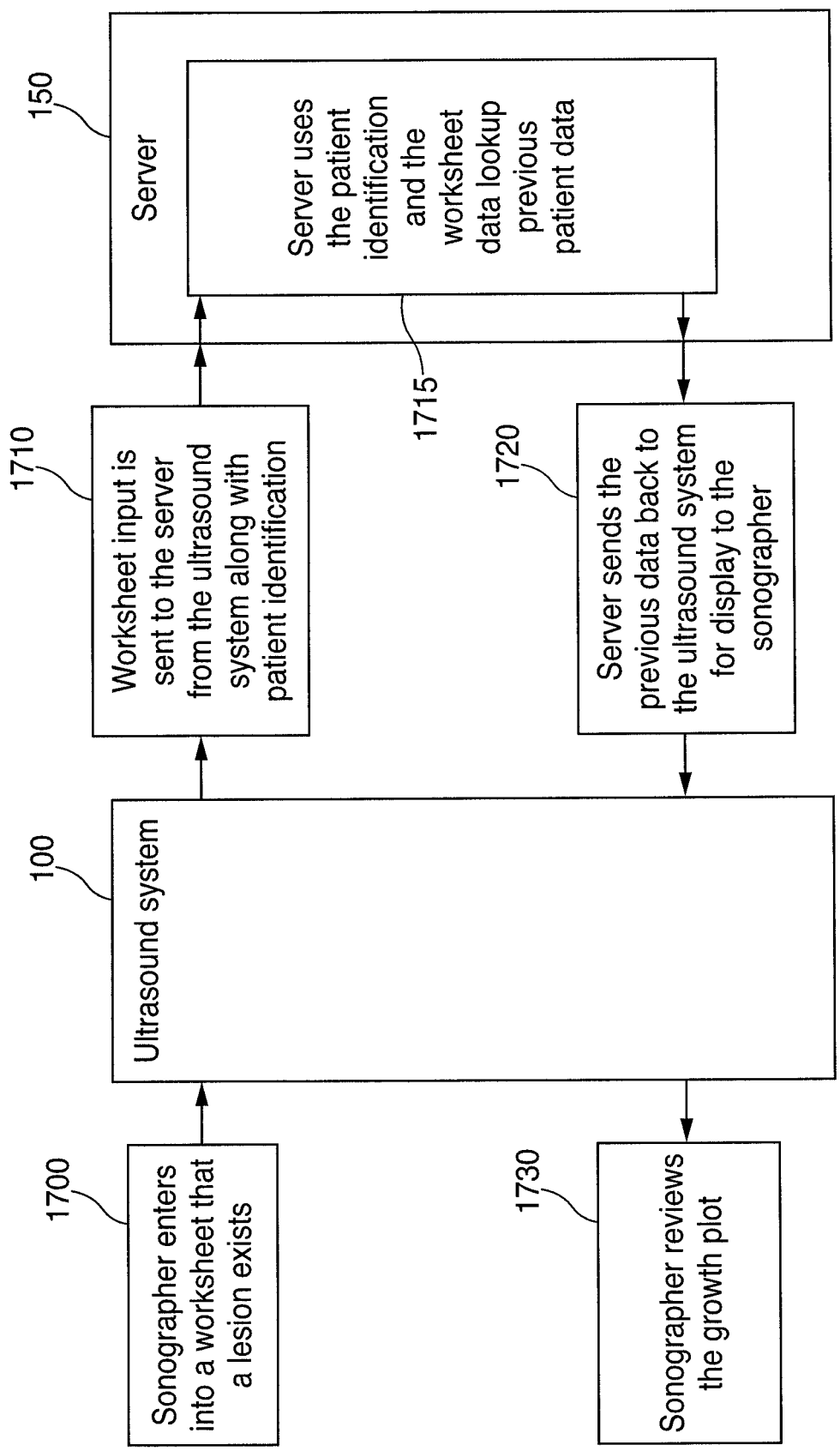
FIG. 17 is an illustration of an embodiment in which a server returns data in response to a worksheet entry.

As another example, as a sonographer is filling-out a patient study worksheet on the medical diagnostic ultrasound imaging system 100, the information completed on the worksheet can be sent to the server 150. The server 150 can process the information to determine what remaining sections of the worksheet are relevant and only return the relevant remaining sections to the medical diagnostic ultrasound imaging system 100. As a related additional example, consider a situation in which the sonographer indicates on a patient study worksheet that there is a cyst on the patient's liver, and that information is sent to the server 150. In response to this information, the server 150 can modify the patient study worksheet to include fields asking for the diameter of the cyst and whether the cyst is clear or contains debris. By receiving this modified worksheet on the ultrasound system 100, the sonographer can be guided on next steps during the examination. As yet another example (see FIG. 17), after the sonographer enters into a worksheet that a lesion exists (act 1700), the worksheet input, along with the patient identification, is sent to the server 150 (act 1710). The server 150 uses the patient identification and the worksheet data to look-up previous patient data (act 1715) and returns it for display and use by the sonographer (acts 1720 and 1730).

Also, while each diagram discussed above may show a single instance of "first information" sent from the medical diagnostic ultrasound imaging system 100 and a single instance of "second information" sent from the server 150, as noted above, there can be multiple sequences of "first information" sent from the medical diagnostic ultrasound imaging system 100 and multiple sequences of corresponding "second information" sent from the server 150. This provides multiple instances of interactivity that can improve workflow. Also, the various instances of "first information" can be sent at different points during the examination. For example, patient identification information can be sent to the server 150 at the very start of the examination, whereas a measure of anatomy can be sent to the server 150 at some point after the start of the examination.

It should also be noted that, in one embodiment, the functionality of interacting with the server 150 is performed by a controller 230 integrated in the medical diagnostic ultrasound imaging system 100. As such, the functionality of interacting with the server 150 is portable with the medical diagnostic ultrasound imaging system 100 and does not require an additional computer local to the medical diagnostic ultrasound imaging system 100 (e.g. a separate network-connected computer in the examination room). Also, although the medical diagnostic ultrasound imaging system 100 interacts with the server 150, it is more than just a substitute for a computer terminal, as a computer terminal does not both generate ultrasound images and accept sonographer measurements made using electronic calipers on the ultrasound machine, sonographer observations, etc. That is, having one system being used to both conduct the examination and interact with the server provides advantages over using two separate devices.

There are many alternatives and additions that can be used with these embodiments. For example, there can be instant messaging between the operator of the medical diagnostic ultrasound imaging system and a physician or other person, which can provide an efficient communication mechanism. For example, the operator can enter a message into the medical diagnostic ultrasound imaging system, and the medical diagnostic ultrasound imaging system can send the message to a physician or other person (e.g., via the server or via another communication channel). The message can include text entered by the operator and/or other information, such as, but not limited to, a reference to a patient, a reference to a study, a reference to one or a few medical images previously "tagged" by the sonographer for comment by the physician, or a reference to the entire exam up to this point in time. The physician or other person receiving the message can then send a response back to the operator (e.g., via the server or via another communication channel) that can provide direction or guidance to the sonographer on how to complete the exam.

Also, as noted above, communication between the medical diagnostic ultrasound imaging system and the server can occur in a variety of ways. The following paragraphs describe embodiments in which two different communication channels are used for this communication. In this embodiment, communication via one of the communication channels occurs within a predetermined amount of time (e.g., one second or less, five seconds or less, ten seconds or less, thirty seconds or less). This predetermined amount of time may allow faster communication than via the other communication channel (e.g., a DICOM channel). Also, in one embodiment, the controller of the medical diagnostic ultrasound imaging system is configured to send and receive different information via the first communication channel than via the second communication channel. Some or all of these features may be important to providing the improvements in workflow discussed above, as slower and/or non-deterministic communication channels may not timely provide information during the examination of a patient. With this by way of background, the following paragraphs provide more information and examples.

Medical ultrasound systems are often network connected to servers using the DICOM protocol. The network connection may be a physical cable or wireless (e.g., WiFi). The DICOM protocol is an International Standard (the Standard) for the transfer of information between medical devices. The DICOM protocol combined with the network creates a communication channel (the DICOM channel) between the ultrasound system and the server. The Standard defines the type of information that can be transferred. For example, the standard defines how to transfer ultrasound images between an ultrasound system and a storage server. The type of information transferred on the DICOM channel is limited by the DICOM standard. The Standard also defines how the information is transferred.

Figure 18:
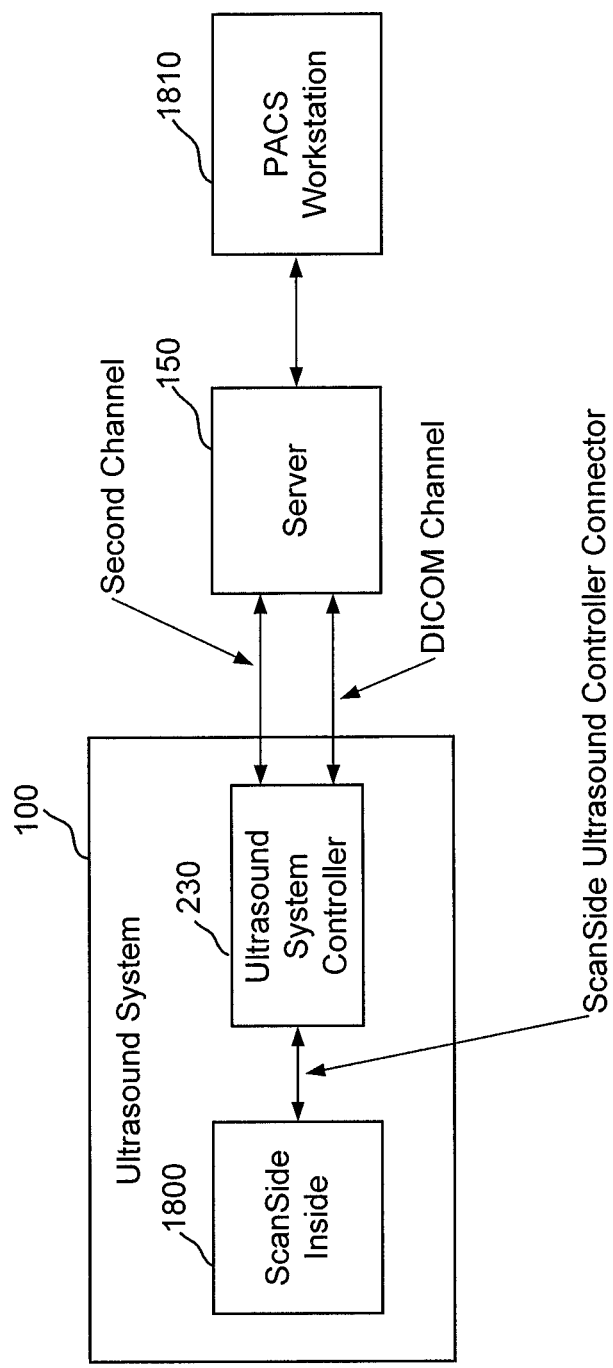
FIG. 18 is a block diagram of a medical diagnostic ultrasound imaging system and server of an embodiment.

The embodiment adds a second channel of communication between the ultrasound system 100 and the server 150 (see FIG. 18). This channel provides for the transfer of information that may not be included in the DICOM standard and for transferring information in ways that may not be supported by the DICOM standard. The second channel can use transfer mechanisms that are faster, more flexible, and/or more responsive than DICOM implementations. In one example, the second channel is not a replacement for the DICOM channel—it is a supplement and works alongside the DICOM channel. Thus, in this example, both the DICOM channel and the second channel are used. In other examples, a single channel may be used.

The DICOM channel and the second channel may both use the same network connection as networking standards support multiple simultaneous channels using different protocols. Alternatively, they may use different communication connections (e.g., the DICOM channel might use an ethernet cable, while the second channel might use a USB cable).

DICOM is typically not real time or deterministic (e.g., the time that information takes to transfer between the ultrasound system and server is not predetermined and may vary during normal operation). DICOM assures accurate, error-free transmission of data but does not assure delivery on a set time schedule. The second channel can operate (e.g., in a real-time or near real-time mode, which can be one second or less) with guaranteed delivery times.

Consider the following as an example. Measurements are often made in the process of performing an ultrasound exam. For example, if a thyroid nodule is seen on an image, the sonographer can use electronic calipers to measure the size of the nodule. These measurements may be transferred by DICOM using a part of the Standard called Structured Reporting. The transfer usually occurs at the end of the exam. Transfer of the measurement in real time, during the exam, using the second channel provides benefits. The sonographer can compare the measurement to prior measurements in prior studies and determine if the current measurement is consistent with prior measurements. If it is not consistent, the sonographer can repeat and correct the measurement before moving on to other parts of the exam. Without the second channel, the sonographer will have to wait until the end of the study to compare a measurement. If it should be repeated, it is more time consuming because the sonographer needs to go back in the exam room and possibly reposition the patient and change scanner settings.

As another example, many modern ultrasound systems provide capabilities to define and use Scan Protocols to guide and control scanning. Multiple protocols are supported by a system with each protocol associated with a particular type of exam. There might be one protocol associated with a carotid study and another associated with an abdominal study. A protocol consists of a series of image acquisition and measurement steps. An abdominal protocol might have steps to observe, measure, and acquire images of the liver, kidneys, and spleen. In a system with a second channel, the second channel can communicate to the server the current protocol step. This information can be used to display the appropriate findings entry form to the sonographer. When the scan protocol step changes to the liver, a message can be sent over the second channel, which can cause the liver form to be displayed automatically. When the scan protocol step changes to kidney, the form can change to the kidney form. Without the second channel, the sonographer would have to manually change forms. The second channel can be used in a reverse manner to allow the sonographer to change forms and have the form change set the ultrasound system scan protocol step. This forward and backward communication over the second channel synchronizes the display of findings entry forms and ultrasound scan protocol steps.

Listed below are additional examples of the second channel and information transferred over that channel.

| Information Sent Over the Second Channel | Direction | Result |
| --- | --- | --- |
| Measurement Acquired Description of the measurement Measurement Value Identifier of the image that was measured The image that was measured | Ultrasound to Server | The server responds by sending information to the ultrasound system - including any of the following corresponding measurements from prior studies for comparison corresponding images from prior studies for comparison (e.g.,are the calipers placed in the same place as on prior studies?) the identifier tags the measurement to the measured image and enables the reading physician to quickly navigate from a measurement to viewing the measured image |
| Image Flagged Identifier of the image that was flagged Study Started Study Ended Protocol Step Changed on the ultrasound system Protocol Step Changed on the server | Ultrasound to Server | The flagged image set is a visual summary of the study used by the radiologist to gain a rapid understanding of the sonographers findings |

Turning again to the drawings, FIG. 18 is a block diagram of a medical diagnostic ultrasound imaging system 100 and server 150 of an embodiment. As shown in FIG. 18, the medical diagnostic ultrasound imaging system 100 comprises a system controller 230, which controls various functions of the medical diagnostic ultrasound imaging system 100, as discussed above. A first communication channel (here, a DICOM channel, although other types of channels can be used) and a second communication channel connect the controller 230 and the server 150.

The second communication channel provides bidirectional communication between the ultrasound system 100 and the server 150 and communicates information that is not typically communicated over the DICOM channel and provides real-time (or near-real-time) communication, deterministic communication, and/or faster communication than the DICOM channel.

As also shown in FIG. 18, the medical diagnostic ultrasound imaging system 100 contains a module labeled "ScanSide Inside" 1800. This module, which is in communication with the controller 230 (e.g., via a ScanSide—Ultrasound Controller connector), provides input/output functionality for the communication with the server 150 to provide the workflow improvements discussed above. A "module" may take the form of a packaged functional hardware unit designed for use with other components, a portion of a program code (e.g., software or firmware) executable by a (micro)processor or processing circuitry that usually performs a particular function of related functions, or a self-contained hardware or software component that interfaces with a larger system, for example.

The ScanSide module 1800 may be implemented in various ways. For example, in one embodiment, the ScanSide module 1800 is implemented as a "thin client" (e.g., web browser) interface to the server 150. As another example, the ScanSide module 1800 can be implemented using a Remote Desktop Protocol. The user can interact with the ScanSide module 1800 using a user input device, such as a trackball, keyboard, touch screen, and/or display screen of the ultrasound system 100. In one embodiment, it will appear to the user as if the ScanSide functionality is running on the ultrasound system 100 but, in fact, the functionality is running on the server 150, and the trackball and keyboard input are passed to the server 150, and the screen display is generated on the server 150 and displayed on the ultrasound system 100. The ScanSide Ultrasound Controller connector shown in FIG. 18 can send the trackball and keyboard input to the server 150, and the server 150 can use this connection to send the screen display back to the ultrasound system 100. Also, while communication to/from the ScanSide module 1800 is seen going through the ultrasound system's controller 230, in other embodiments, communication to and/or the ScanSide module 1800 can avoid going through the ultrasound system's controller 230. Also, the ScanSide module 1800 can be integrated into the controller 230, such as when a one or more processors execute computer-readable program code that implements both the functionality of the ScanSide module 1800 and the functionality for operating the ultrasound system 100. Accordingly, for simplicity, this document might use the term "controller" to refer to the ScanSide module 1800 alone or to the ScanSide module 1800 in the combination with the ultrasound controller 230.

Figure 19:
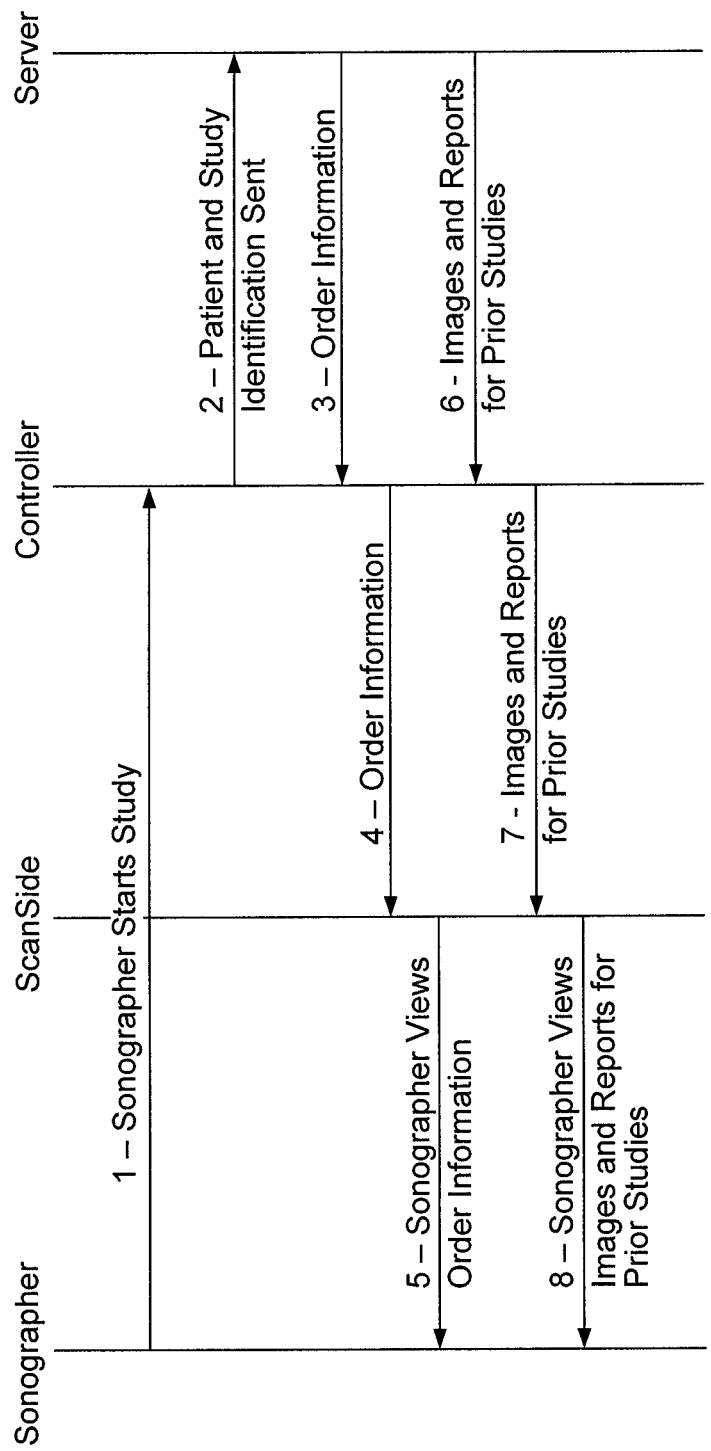
FIG. 19 is a flow chart of a method of an embodiment showing communication on a second communication channel before the start of image acquisition.

The following paragraphs provide examples of how the second channel can be used. Returning to the drawings, FIG. 19 is a flow chart of a method of an embodiment showing communication on the second communication channel before the start of image acquisition. More specifically, FIG. 19 shows the sequence of the second channel messages that occur when the sonographer starts a study.

As shown in FIG. 19, the steps in this method comprise:

1. The operator interacts with the controller 230 to start a new study.

2. The controller 230 sends study identification information to the server 150. This information identifies the Patient and Study. Patients are usually identified by a patient "medical record number," and studies are usually identified by a study "accession number."

3. The server 150 communicates with the controller 230 to load the Order for the started study.

4. The controller 230 communicates with the ScanSide module 1800 to load the Order on the ScanSide module 1800.

5. The Sonographer views the Order on the ScanSide module 1800.

6. The server 150 sends prior study images and reports to the controller 230.

7. The controller 230 sends the prior images and reports to the ScanSide module 1800.

8. The Sonographer views the prior images and reports on the ScanSide module 1800.

The messages 2, 3, and 6 between the controller 230 and the server 150 are transported by the second channel. These messages significantly improve sonographer efficiency and accuracy.

The second channel messages can provide several improvements. For example,

Order information can be transferred to the ScanSide module 1800, so that the sonographer can read the Order at the ultrasound system 100. The Order indicates the name of the physician who ordered the study, why the study was ordered, and what type of study was ordered. If the Order is not available at theScanSide module, the sonographer may have to go to a separate computer to read the Order. This is inefficient and time-consuming. As another example, the display of images and reports from prior studies provides an advantage. If these are not available at the ScanSide module 1800, the sonographer may need to go to a separate computer to review images and reports from prior studies. In this case, the sonographer would have to remember the images and reports while performing the study. Using the second channel puts the images and reports on the ScanSide module 1800, so that they can be reviewed during the study, and the sonographer does not have to rely on memory.

Figure 20:
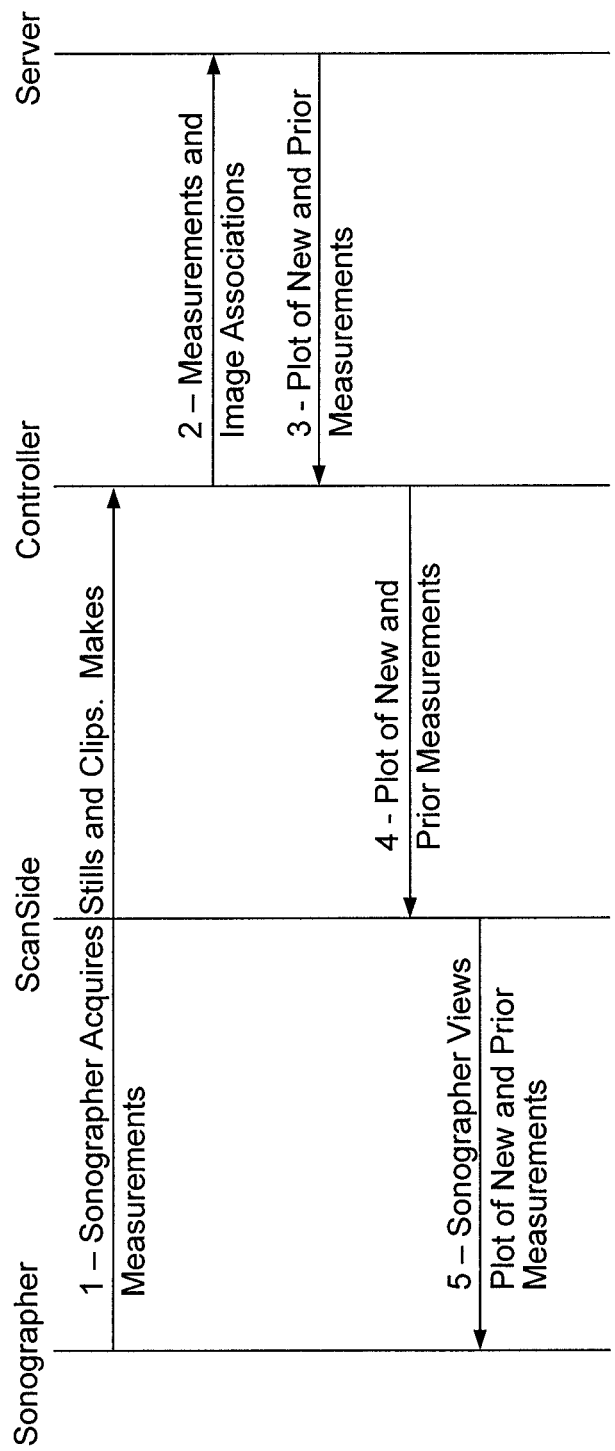
FIG. 20 is a flow chart of a method of an embodiment showing communication on a second communication channel during image acquisition to generate a measurement plot.

FIG. 20 provides another example implementation and shows communication on the second communication channel during image acquisition to automatically generate a plot of a measured value. These messages are sent during the image acquisition phase of a study.

The steps in this method comprise:

1. The sonographer acquires stills and clips and makes measurements on the acquired images.

2. Measurements and Study Associations are sent from the controller 230 to the server 150 by the second channel. Measurements are sent by messages that contain the measured value, the measurement units, a description of what was measured, and an identification of which image was measured. For example, in a thyroid exam, the measurement information might be: measured value is 2, measurement units are centimeters, description is the width of nodule 2, and image identification is the unique identifier of the image.

3. The server 150 processes this information to generate a plot showing the current and prior measurements of the width of nodule 2. An image of the plot is sent from the server 150 to the controller 230.

4. The controller 230 sends the plot image to the ScanSide module 1800.

5. The Sonographer views the plot image displayed by the ScanSide module 1800.

This method can be very beneficial to the sonographer. By viewing the plot, the sonographer can see if the measurement makes sense or if an error might have occurred during measurement. For example, if the current value is less than the prior value, it is likely that the sonographer has made an error because thyroid nodules rarely decrease in size. Seeing this information directly after making a measurement is very useful since if an error is suspected, it is much easier to correct it directly after making a measurement. Without the second channel, the information needed to generate a plot would not be available during the study, and the plot would be seen at the end of the study. The sonographer would then need to set up to make the measurement again. This is time-consuming.

Figure 21:
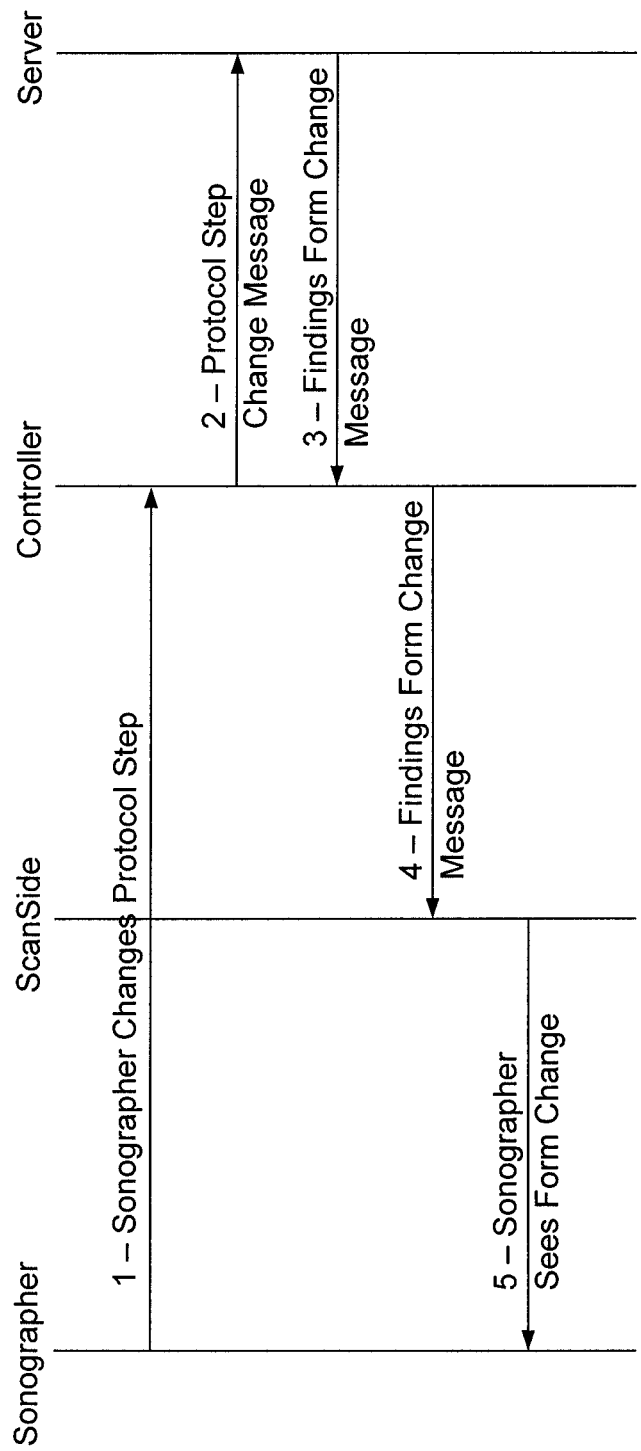
FIG. 21 is a flow chart of a method of an embodiment showing communication on a second communication channel during image acquisition to automatically change a findings form in response to a protocol step change.

FIG. 21 provides another example implementation and is a flow chart of a method of an embodiment showing communication on a second communication channel during image acquisition to automatically change a findings form in response to a protocol step change. This figure shows the workflow associated with scan protocol step changes driving changes in findings entry forms. This workflow depends on second channel messages between the controller 230 and the server 150.

The steps in this method are:

1. The sonographer changes the scan protocol step on the ultrasound system 100. For example, the scan protocol may be an abdominal protocol, and the step might change from kidney to liver.

2. The controller 230 sends a message to the server 150 that describes the protocol step change. Using the example above, the message will indicate that the protocol step changed from kidney to liver. This means that the sonographer has completed scanning the kidney and is starting scanning the liver.

3. The controller 230 sends the form for entering information that fits the step change to the controller 230. In the example above, this will be a form for entering findings that relate to the liver.

4. The controller 230 sends the form to the ScanSide module 1800.

5. The ScanSide module 1800 displays the form, so that the sonographer can enter findings into the form.

This set of messages automatically synchronizes the display of findings entry forms with scan protocol step (messages 2 and 3 are second channel messages). This improves workflow efficiency. Without this automatic synchronization, the sonographer may need to manually change forms every time the scan protocol step is changed.

Figure 22:
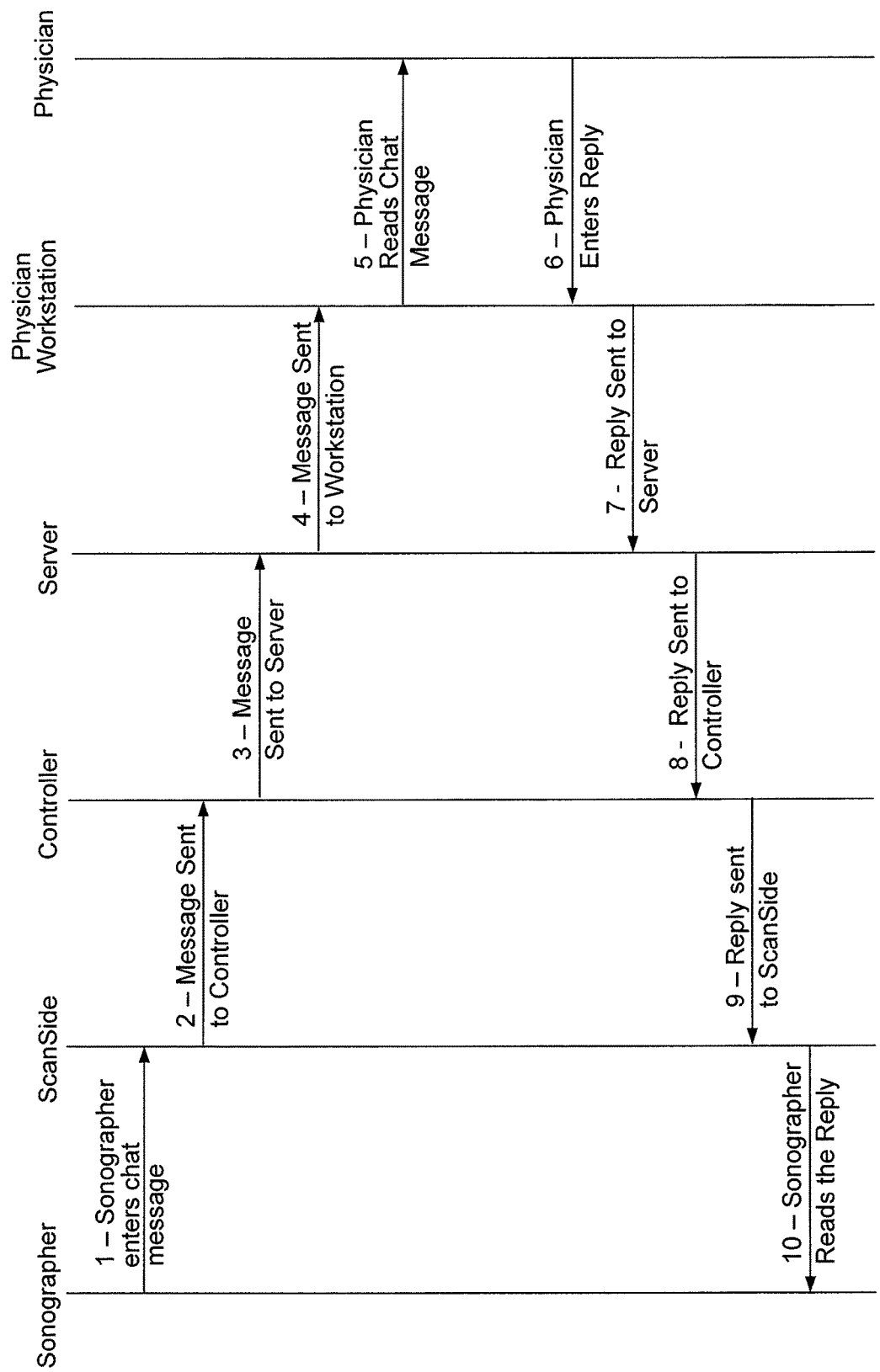
FIG. 22 is a flow chart of a method of an embodiment showing communication between a sonographer and a physician on a second communication channel.

As yet another example implementation, FIG. 22 is a flow chart of a method of an embodiment showing communication ("chatting") between a sonographer and a physician on the second communication channel. This figure shows the sequence of second channel messages when a sonographer sends a chat to a physician and the physician replies. This chat capability is dependent on the second channel.

This method comprises the following steps:

1. The sonographer enters a chat message on the ScanSide module 1800.

2. The chat message is sent to the controller 230.

3. The controller 230 sends the message to the server 150.

4. The server 150 sends the message to the physician workstation 1810.

5. The physician reads the chat on the workstation 1810.

6. The physician enters a reply on the workstation 1810.

7. The reply is sent to the server 150.

8. The server 150 uses the second channel to send the message to the controller 230.

9. The controller 230 sends the message to the ScanSide module 1800.

10. The Sonographer reads the reply on the ScanSide module 1800.

Chat capabilities can provide several advantages. Without chat, sonographers communicate with physicians by leaving the scan exam room and walking to where the physicians are located or by calling on the telephone. Both methods are inefficient and leave the patient unattended for a period of time.

As can be seen by these examples, these embodiments transform the ultrasound system 100 into a different machine. Specifically, standard ultrasound systems without the second channel are used only to acquire images (stills and clips) and make measurements. They are only a diagnostic imaging system. With the second channel, the ultrasound system is transformed into a system that provides data to the sonographer to guide the study and into a communication tool. Without the second channel, the sonographer would need to get this information from other sources and is unable to access it during the exam. Access during the exam is very important to guide the exam. Also, as described above, the second channel adds a communication capability to the ultrasound system 100. Without this capability, the sonographer must rely on verbal communication—either face-to-face on via telephone.

It should be noted that the various implementations discussed above are merely examples, and other implementations can be used. For example, while the above paragraphs described certain types of information conveyed on the second channel, other types of information can be conveyed. Without intending to be a limitation, such additional types of information can include, but are not limited to, yes-no findings and multiple choice findings.

Examples of yes—no findings include, but are not limited to, (a) Liver—Portal Veins—Normal direction of flow?, (b) Gallbladder—Gallstones?, (c) Kidney—Hydro nephrosis?, (d) Kidney—increased echogenicity, (e) Spleen—Enlarged?, (f) Spleen—small calcifications consistent with granulomata?, (g) Aorta—abdominal aortic aneurysm?, (h) Aorta—atherosclerotic changes without aneurysm?, (i) Kidney cyst, (j) Liver mass, (k) Thyroid nodules, (l) Pancreatic duct stone(s), (m) Ovary—surgically absent?, (n) Prostate—Enlarged?, (o) Scrotal—varicocele, (p) Scrotal—Hydrocele, (q) Scrotal—wall thickening, (r) Bladder—Post void volume—none, small, moderate, large, (s) Bladder—Ureteral jets—bilateral, right only, left only, (t) Renal—surgically removed, (u) Renal—Hydro nephrosis? Mild, moderate, severe, (v) Renal—Resistive index—normal/elevated, (w) Chest—Pleural Effusion?, (x) Chest—Thoracentesis—site mark only/guided, and (y) Intracranial hemorrhage—right/left/bilateral.

Examples of multiple choice findings include, but are not limited to, (a) Liver—Cyst location?—Right lobe, left lobe, Upper, Middle, Lower, (b) Gallbladder wall?—Normal, thickened, (c) Kidney doppler—Resistive index?—Normal, elevated, (d) ACR TIRADS—Nodule composition—Mixed cystic and solid, cystic, spongiform, solid, (e) ACR TIRADS—Nodule echogenicity—anechoic, hyperechoic, isoechoic, hypoechoic, (f) ACR TIRADS—Nodule margins—smooth, ill-defined, lobulated, irregular, extra-thyroidal extend, (g) Thyroid gland—enlarged, diffusely heterogeneous, nodules, (h) Pelvic reason for Transabdominal— for global imaging, for fibroid uterus, (i) Pelvic reason for transvaginal—bladder not filled, more detail visualization of ovaries, more detailed visualization of endometrium, (j) Adnexal lesion—Simple cyst, complex cyst, hydrosalpinx, solid mass, (k) Ovarian complex cyst(s)—internal echoes, fine septations, thick septations, irregular wall, thick-walled, (l) Prostate—lesion side, right/Left, (m) Prostate—lesion location, Apex/Base, (n) Prostate calcifications—right/left, junction of central and peripheral zone, in central gland, in peripheral zone, (o) Testicular size—enlarged, small (atrophic), (p) Testicular echogenicity—hypoechoic, hyperechoic, heterogeneous, (q) Testicular—microlithiasis, dilated rete testis, (r) Renal calculi—upper pole, mid pole, lower pole, renal pelvis, UPJ, (s) Pancreatic mass—Head, body, tail, (t) Chest—Pleural Effusion size—small, moderate, large. With septations?, and (u) Neonatal Head—Intracranial hemorrhage—germinal matrix, intraventricular, parenchyma.

Additional examples of information sent on the second channel from the ultrasound system 100 to the server 150 include, but are not limited to: (a) Flagged image—sent from the ultrasound system 100 to the server 150 to indicate that an image is marked as important with a flag—image is identified by a unique identifier, (b) Measurement tagged to image—sent from the ultrasound system 100 to the server 150 to indicate that a particular measurement was made on a particular image—image is identified by its unique identifier, (c) Study started—this message goes from the ultrasound system 100 to the server 150 and indicates that a new study has been started on the ultrasound system 100—the message identifies the study by the study accession number which is a unique number identifying the study and by the patient record number which is a unique number identifying the patient, (d) Study closed—this message goes from the ultrasound system 100 to the server 150 and indicates that a study has been ended. The study is identified by the study accession number, (e) Show/hide ScanSide—this message goes from the ultrasound system 100 to the server 150. A show message indicates that the ScanSide window on the ultrasound system 100 should be made visible to the user and a hide message indicates that the ScanSide window should be hidden, (f) Protocol step change on ultrasound system 100—this message goes from the ultrasound system 100 to the server 150 and indicates that the scan protocol step has changed. In response to this message, the server 150 may change the findings entry display on the ultrasound system 100, and (g) Image acquired—this message goes from the ultrasound system 100 to the server 150 and indicates that an image has been acquired.

Additional examples of information sent on the second channel from the server 150 to the ultrasound system 100 include, but are not limited to: (a) Protocol step change from the server 150—this message goes from the server 150 to the ultrasound system 100 and indicates that the ultrasound system 100 should change the active protocol step, (b) Prior study image, (c) Prior study drawing, and (d) Prior study report.

It should also be noted that while the first channel has been referred to as a DICOM channel in several of the above examples, the first channel can operate under a standard other than DICOM. However, when DICOM is used, the following are examples on information that can be exchanged over the first communication channel:

| DICOM Service Class | SCU Request | SCP Response | Note |
| --- | --- | --- | --- |
| Storage Service Class | Request to store an ultrasound image | Success, failure or rejection | The Request includes the image |
| Storage Service Class | Request to store an Structured Reporting object | Success, failure or rejection | The Request contains the Structured Reporting object that contains measurement values. |
| Modality Worklist Service Class | Request to send the modality worklist | Sends the list or failure or reject | The modality work list is a list of scheduled studies with information about each of the schedule studies. |
| Print | Request to have specified images printed on a printer | Success, failure or rejection | |

The ultrasound system 100 acts (in DICOM terminology) as a Service Class User (SCU), and the server 150 acts as a Service Class Provider (SCP). The SCU initiates communication with the SCP. The SCU sends a request to the SCP, and the SCP responds to that request. DICOM communication is not real-time because of how it is implemented. Requests are sent and information is returned, but there is no guarantee of response time. This is a characteristic of DICOM implementations and one of the reasons why a second channel provides advantages. Another reason for the second channel is that DICOM does not support some of the information that can be sent send over the second channel.

Finally, although a medical diagnostic ultrasound imaging system was used above as an example to illustrate these embodiments, it should be noted that these embodiments can be implemented in other medical diagnostic imaging system. Examples of other imaging modalities include, but are not limited to, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. Further, the phrase "medical diagnostic" is used herein to distinguish from "therapeutic" systems (e.g., ultrasound system that uses ultrasonic waves to destroy kidney stones). However, it should be noted that these embodiments can be used in therapeutic systems as well.

It is intended that the foregoing detailed description be understood as an illustration of selected forms that the invention can take and not as a definition of the invention. It is only the following claims, including all equivalents, that are intended to define the scope of the claimed invention. Finally, it should be noted that any aspect of any of the preferred embodiments described herein can be used alone or in combination with one another.

What is claimed is:

1. A medical diagnostic ultrasound imaging system comprising:
   at least one transmitter;
   at least one receiver; and
   a controller in communication with the at least one transmitter and the at least one receiver, wherein the controller is configured to communicate with a server via a first communication channel and a second communication channel, and wherein the controller is further configured to send and receive different information via the first communication channel than via the second communication channel;

wherein communication between the controller and the server via the second communication channel occurs within a predetermined amount of time; and wherein the controller is further configured to receive a pre-populated report for a radiologist from the server via the second communication channel, wherein the pre-populated report is responsive to information the controller previously sent to the server via the second communication channel during an examination of a patient.

2. The medical diagnostic ultrasound imaging system of claim 1, wherein the predetermined amount of time is one second or less.

3. The medical diagnostic ultrasound imaging system of claim 1, wherein the predetermined amount of time is five seconds or less.

4. The medical diagnostic ultrasound imaging system of claim 1, wherein the predetermined amount of time is ten seconds or less.

5. The medical diagnostic ultrasound imaging system of claim 1, wherein the predetermined amount of time is thirty seconds or less.

6. The medical diagnostic ultrasound imaging system of claim 1, wherein the first communication channel is a Digital Imaging and Communications in Medicine (DICOM) channel.

7. The medical diagnostic ultrasound imaging system of claim 1, wherein the controller utilizes a thin-client interface for communication in the second communication channel.

8. The medical diagnostic ultrasound imaging system of claim 7, wherein the thin-client interface comprises a web browser interface.

9. The medical diagnostic ultrasound imaging system of claim 7, wherein the thin-client interface comprises a remote desktop protocol.

10. The medical diagnostic ultrasound imaging system of claim 1, wherein the pre-populated report received from the server via the second communication channel is simultaneously displayed with a medical diagnostic ultrasound image generated by the medical diagnostic ultrasound imaging system on one or more display devices of the medical diagnostic ultrasound imaging system.

11. The medical diagnostic ultrasound imaging system of claim 1, wherein the controller is configured to send patient and/or study information to the server via the second communication channel and receive at least one of the following from the server via the second communication channel: order information, an image from a prior study, and a report from a prior study.

12. The medical diagnostic ultrasound imaging system of claim 1, wherein the controller is configured to send a measurement and/or image association to the server via the second communication channel and receive at least one of the following from the server via the second communication channel: a plot of a prior measurement and a plot of a new measurement.

13. The medical diagnostic ultrasound imaging system of claim 1, wherein the controller is configured to send a protocol step change message to the server via the second communication channel and receive a findings form change message from the server via the second communication channel.

14. The medical diagnostic ultrasound imaging system of claim 1, wherein the second communication channel is used for communication between sonographer messages received by the medical diagnostic ultrasound imaging system and a remote physician.

15. A medical diagnostic ultrasound imaging system comprising:
  at least one transmitter;
  at least one receiver; and
  a controller in communication with the at least one transmitter and the at least one receiver, wherein the controller is configured to communicate with a server via a first communication channel and a second communication channel;
  wherein communication between the controller and the server via the second communication channel occurs within a predetermined amount of time; and
  wherein communication between the controller and the server via the second communication channel is faster than communication between the controller and the server via the first communication channel; and
  wherein the controller is further configured to receive a pre-populated report for a radiologist from the server via the second communication channel, wherein the pre-populated report is responsive to information the controller previously sent to the server via the second communication channel during an examination of a patient.

16. The medical diagnostic ultrasound imaging system of claim 15, wherein the controller is further configured to send and receive different information via the first communication channel than via the second communication channel.

* * * * *